(12) United States Patent
Barseghyan et al.

(10) Patent No.: US 11,208,391 B2
(45) Date of Patent: Dec. 28, 2021

(54) POLYMORPHS AND NEW PATH TO SYNTHESIZE TAFAMIDIS

(71) Applicant: AZAD PHARMA AG, Schaffhausen (CH)

(72) Inventors: Karine Barseghyan, Yerevan (AM); Davit Hambardzumyan, Yerevan (AM); Grigor Gevorgyan, Abovyan (AM); Vahuni Karapetyan, Kotayk Marz (AM); Kristine Nerkararyan, Tavush (AM); Thomas Maier, Stockach (DE)

(73) Assignee: AZAD Pharma AG, Schaffhausen (CH)

( * ) Notice: Subject to any disclaimer, the term of this patent is extended or adjusted under 35 U.S.C. 154(b) by 0 days.

(21) Appl. No.: 16/979,261

(22) PCT Filed: Mar. 13, 2019

(86) PCT No.: PCT/EP2019/056317
§ 371 (c)(1),
(2) Date: Sep. 9, 2020

(87) PCT Pub. No.: WO2019/175263
PCT Pub. Date: Sep. 19, 2019

(65) Prior Publication Data
US 2020/0399234 A1 Dec. 24, 2020

(30) Foreign Application Priority Data
Mar. 13, 2018 (GB) ..................................... 1804005

(51) Int. Cl.
*C07D 263/57* (2006.01)
(52) U.S. Cl.
CPC ........ *C07D 263/57* (2013.01); *C07B 2200/13* (2013.01)

(58) Field of Classification Search
CPC .................................................. C07D 263/57
See application file for complete search history.

(56) References Cited

FOREIGN PATENT DOCUMENTS

| WO | 2004056315 A2 | 7/2004 |
|---|---|---|
| WO | 2005113523 A1 | 12/2005 |
| WO | 2009080788 A2 | 7/2009 |
| WO | 2013033258 A1 | 3/2013 |
| WO | 2013038351 A1 | 3/2013 |
| WO | 2013168014 A1 | 11/2013 |
| WO | 2016038500 A1 | 3/2016 |

OTHER PUBLICATIONS

Griesser: "Chapters. The Importance of Solvates" In: "Polymorphism in the Pharmaceutical Industry", 2006, Wiley-VCH, Weinheim (DE), XP055582446, ISBN: 978-3-527-31146-0, pp. 211-215, p. 211, paragraph 1.
Bernstein: "Chapter 1.2.1 Polymorphism" In: "Polymorphism in Molecular Crystals", 2002, Clarendon Press, Oxford, GB, XP055582436, ISBN: 978-0-19-850605-8, pp. 2-4, p. 2, penultimate paragraph; p. 4, paragraph 3, last sentence.
Caira: "Crystalline Polymorphism of Organic Compounds", Topics in Current Chemistry, vol. 198, 1998, pp. 163-208, XP008166276, ISSN: 0340-1022, Paragraph bridging pp. 165 and 166.
Byrn et al.: "Pharmaceutical Solids: A Strategic Approach to Regulatory Considerations", Pharmaceutical Research, vol. 12, No. 7, Jan. 1, 1995 (Jan. 1, 1995), pp. 945-954, XP055531015, DOI: 10.1023/A:1016241927429, Abstract; p. 946, right col. paragraphs 2, 3.

*Primary Examiner* — Shawquia Jackson

(57) ABSTRACT

The present invention relates to a new path to synthesize crystalline Tafamidis polymorphs starting from a Tafamidis acetic acid adduct. In addition, this invention relates to a process to synthesize Tafamidis (2-(3,5-dichlorophenyl)-1,3-benzoxazole-6-carboxylic acid * (2R,3R,4R,5S)-6-(methyl-amino)-hexane-1,2,3,4,5-pentol), new Tafamidis crystalline polymorphs, a pharmaceutical compositions comprising the new crystalline polymorphs and to the therapeutic use of such new polymorphs.

17 Claims, 17 Drawing Sheets

POLYMORPHS AND NEW PATH TO SYNTHESIZE TAFAMIDIS

CROSS-REFERENCE TO RELATED APPLICATIONS

This application is a U.S. National Phase Application under 35 U.S.C. 371 of International Application No. PCT/EP2019/056317, filed on Mar. 13, 2019, which claims the benefit of Great Britain Patent Application No. 1804005.5, filed on Mar. 13, 2018. The entire disclosures of the above applications are incorporated herein by reference.

FIELD OF THE INVENTION

The present invention relates to a new path to synthesize crystalline Tafamidis polymorphs starting from a Tafamidis acetic acid adduct. In addition, this invention relates to a process to synthesize Tafamidis (2-(3,5-dichlorophenyl)-1,3-benzoxazole-6-carboxylic acid * (2R,3R,4R,5S)-6-(methyl-amino)-hexane-1,2,3,4,5-pentol), new Tafamidis crystalline polymorphs, a pharmaceutical compositions comprising the new crystalline polymorphs and to the therapeutic use of such new polymorphs.

BACKGROUND

Tafamidis is a drug used for the treatment of transthyretin-related hereditary amyloidosis.

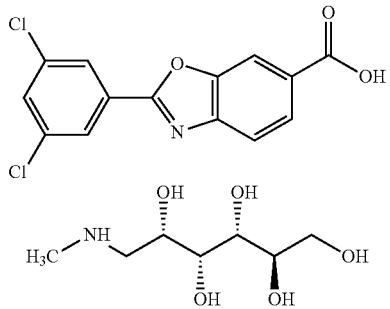

Transthyretin is a homotetrameric protein present in serum and cerebral spinal fluid and the main function is the transport of L-thyroxine and the holo-retinol-binding-protein. The drug is used in the form of a meglumine salt and functions by kinetic stabilization of the correctly folded tetrameric form of the protein. In the pathologic state the protein dissociates under denaturating conditions and the following monomer unfolding enables amyloid fibril formation, causing finally a failure of the autonomic nervous and/or the peripheral nervous system. The treatment slows the dissociation of the native protein and consequently amyloid fibril formation and degeneration of post-mitotic tissue is delayed.

The fundamental concept for the use of Tafamidis was inter alia described in WO 2004/056315 A2. This patent document reveals that the kinetic stabilization of the native state of transthyretin is an effective mechanism for preventing protein misfolding and that inhibiting of misfolding can be used as an effective treatment or prophylaxis for such diseases. The patent document further discloses treatment and screening methods, as well as specific transthyretin stabilizing compounds.

In addition, a further patent document is specially directed to crystalline solid forms of 6-carboxy-2-(3,5-dichlorophenyl)-benzoxazole. WO 2016/038500 A1 is for instance related to solid forms of 6-carboxy-2-(3,5-dichlorophenyl)-benzoxazole and to methods for their preparation. The teaching also includes pharmaceutical compositions containing at least one solid form and the therapeutic or prophylactic use of such solid forms and compositions.

A specific crystalline form of 6-carboxy-2-(3,5-dichlorophenyl)-benzoxazole meglumine is in addition disclosed in WO 2013/038351 A1. Said crystalline form has a powder X-ray diffraction pattern comprising peaks at diffraction angles (2θ) of 10.7±0.2, 11.8±0.2, and 13.3±0.2.

Nevertheless, besides the existing routes of synthesis and the known solid forms of Tafamidis there is still the need for further routes and polymorphs, which are able to deliver high quality crystalline Tafamidis polymorphs in a reproducible and environmentally friendly way. Furthermore, there is also the need for new Tafamidis meglumine polymorphs comprising superior production properties especially with respect to handling and in tableting.

BRIEF DESCRIPTION OF THE INVENTION

Above mentioned problem is solved according to the invention by a process for the production of crystalline Tafamidis polymorphs, at least comprising the steps of:

a) Forming a dispersion by contacting a Tafamidis acetic acid adduct (E) and a solvent capable of removing the acetic acid adduct molecule from the Tafamidis;

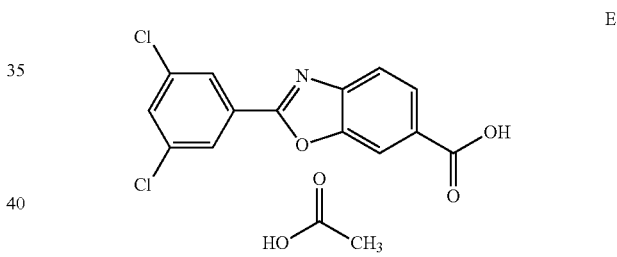

b) Heating the dispersion obtained in step a) and c) Precipitation and drying of the precipitate to yield the crystalline Tafamidis polymorph. Surprisingly, it has been found that it is possible to generate different crystalline Tafamidis polymorphs by starting from a Tafamidis acetic acid adduct. The exchange of the adduct molecule can be achieved in a very gently routine and the resulting products comprise a high level of crystallinity. The resulting products comprise very reproducible physical, chemical and biological properties and the amount of unwanted by-products is very low. This founding is surprising, because it cannot be expected that starting from a single adduct different crystalline polymorphs are accessible. This is surprising, because the thermodynamic and the kinetic side conditions of the polymorph forming process can be expected to be different for different adducts, usually resulting in highly specialized crystallization routines. Albeit, the chemical and sterically differences of the adduct molecules, the applicants were able to establish a very flexible process for the generation of the different adducts with advantages in terms of process chemistry as well as purity of the involved intermediates and products.

A crystalline Tafamidis polymorph according to the invention is substance at least comprising Tafamidis and comprising crystalline properties. The polymorph comprises crystalline properties in cases, wherein an X-ray experiment, as disclosed in the experimental section, comprises distinct X-ray peaks instead of an amorphous halo, only. Thus, the crystalline polymorph comprises an ordered structure in comparison to an amorphous substrate lacking theses ordered structures. The polymorph may comprise only ordered Tafamidis molecules or may comprise further adduct molecules, in close contact to the Tafamidis and forming crystalline, i.e. at least partially regular structures.

In process step a) a dispersion is formed by contacting a Tafamidis acetic acid adduct (E) and a solvent capable of removing the acetic acid adduct molecule from the Tafamidis. The first process step includes the use of a Tafamidis acid adduct. The term adduct means, that a compound is used, wherein acetic acid is bound to the Tafamidis either in the form of a free base or altered e.g. protonated. The bonding between the acetic acid and the Tafamidis free base can be based on van der Waals-interactions or hydrogen bonding between the functional groups of both molecules. The achieved acetic acid Tafamidis adduct can also be classified or named acetic acid solvate. In addition, without being bound by the theory it seems appropriate to assume that the relative orientation of the acetic acid and the Tafamidis in the adduct/solvate is highly reproducible, favoring the generation of crystalline ordered structures of said adduct. Nevertheless, the adduct may be crystalline or amorphous. The adduct is contacted with a solvent. The latter may be achieved by dispersing the dry Tafamidis acetic acid adduct in a solvent under stirring. The solvent may just be used in the process to break the adduct bonds in the Tafamidis acetic acid adduct or it is also possible that the solvent molecule is able to form an adduct with the Tafamidis itself. A solvent capable of removing the acetic acid from the Tafamidis molecule and hence separating the different adduct molecules can for instance be regarded as a solvent capable of dissolving the acetic acid adduct under stirring or under the process conditions of step b), i.e. by additionally applying heat to the dispersion. Solvents which are unable to dissolve the adduct are usually unsuitable for this first process step. Preferably the solvent is able to dissolve at least 90 weight-%, more preferred more than 95 weight-%, and even more preferred more than 97 weight-% of the used Tafamidis acetic acid adduct under the conditions in process step b). The relation between undissolved and dissolved adduct can for instance be determined gravimetrically at 50° C. after an equilibrium is achieved. A suitable temperature range for the process step a) can be ≥0° C. and ≤50° C.

In process step b) the dispersion obtained in step a) is heated. This process step is performed in order to facilitate the adduct interchange. This step may include the application of heat up 125° C. and is preferably achieved by refluxing the dispersion in the given solvent. The dispersion step enables a very efficient processing at short reaction times and a very low amount of unwanted by-products up to this temperature. Thus, high overall yields are obtainable. This is an advantage compared to the state of the art processes, which perform the reactions in a different chemical surrounding at higher temperatures.

In process step c) a precipitate is formed and the precipitate is dried to yield the crystalline Tafamidis polymorph. The crystalline polymorph may be achieved by three different drying methods. On the one hand the solvent can be removed while maintaining the temperature, the temperature may be lowered at an unchanged solvent level or the temperature can be lowered at reduced solvents level. It has been found suitable that the precipitation is achieved at an unchanged solvent level by reducing the temperature, preferably below, 50° C., more preferred below 20° C. and even more preferred below 10° C. and a precipitation timescale of at least 5 h, preferred at least 8 h, more preferred at least 12 h for obtaining the crystalline precipitate. After the precipitate is formed it may also be suitable to further dry the solid in vacuum. A possible drying step may include increasing the temperature of the solid material either at atmospheric or at reduced pressure. The crystalline Tafamidis polymorphs resulting from this drying step preferable comprises a residual solvent content below 10 weight-%, preferably below 5 weight-% and further preferred below 0.5 weight-% (solvent molecules forming part of the adduct are not counted). Such residual solvent contents are very suitable in the course of further processing and especially favor the generation of crystalline structures.

In e preferred embodiment of the process the solvent can be selected from the group consisting of water, methanol, ethanol, ethylacetate, pentane, hexane, halogenated or non-halogenated formic acid, halogenated or non-halogenated acetic acid or mixtures of at least two solvents thereof. This solvent group has been found very suitable to allow the adduct interchange and results in the course of the inventive process in the formation of highly crystalline material. The overall yield is very good. In addition, it has been found suitable to use the group comprising acid-groups for the generation of crystalline Tafamidis polymorphs, wherein the solvent molecule becomes part of the adduct. The hydroxyl-groups comprising solvent molecules has been found useful for generating crystalline polymorphs of the free Tafamidis acid or in cases wherein additional adduct components are used.

In a further aspect of the process the solvent can be a mixture of ethyl acetate and water and the resulting crystalline Tafamidis polymorph is crystalline Tafamidis free acid. In cases, wherein the crystalline free acid is the target of the synthesis the use of water/ethyl acetate mixtures has been found very suitable for dissolution of the acetic acid adduct and for the precipitation of the crystalline free acid. In a preferred embodiment the volume ratio of ethyl acetate to water (ethyl acetate:water) can larger or equal to 50:50 and smaller or equal to 95:5. It is further preferred to use a 90:10 ethyl acetate:water mixture to a achieve very high yields and an excellent crystallinity of the free acid.

In a preferred embodiment of the process the solvent can be formic acid and the resulting crystalline Tafamidis polymorph is crystalline Tafamidis formic acid adduct. The inventive process is especially suitable to synthesize crystalline formic acid adducts from the acetic acid adducts. The formic acid can for instance be introduced in the form of a solvent in inventive process. The formic acid is able to disturb the physical/chemical Tafamidis—acetic acid interaction in such a way, that the acetic acid is withdrawn from the adduct. The formic acid is afterwards able to replace the now vacant position and forms a stable, crystalline adduct. Such adduct interchange is surprising, because it could not be expected a priori, that the formic acid results in more stable adducts compared to the acetic acid.

Within a preferred aspect of the process the solvent can be trifluoroacetic acid and the resulting crystalline Tafamidis polymorph is crystalline Tafamidis trifluoroacetic acid adduct. The inventive process is especially suitable to synthesize crystalline trifluoroacetic acid adducts from the acetic acid adducts. The trifluoroacetic acid can for instance be introduced in the form of a solvent in inventive process. The trifluoroacetic acid is able to disturb the physical/ chemical Tafamidis—acetic acid interaction in such a way, that the acetic acid is withdrawn from the adduct. The trifluoroacetic acid is afterwards able to replace the now vacant position and forms a stable, crystalline adduct. Such adduct interchange is surprising, because it could not be expected a priori, that the trifluoroacetic acid results is more stable adducts compared to the acetic acid.

In another preferred characteristic of the process in step a) besides the solvent a further adduct molecule can be added to the dispersion. In addition, it is possible to further enhance the possible range of crystalline adducts or products by adding further molecules to the solvent in step a). Further suitable adduct molecules may be chosen from the group consisting of acids, like sulfonic acids, e.g. methane sulfonic acid, toluene sulfonic acid or trifluoro methane sulfonic acids or higher boiling solvents or combination of at least two different molecules of that list.

In another embodiment of the process in step a) meglumine can be added to the dispersion in step a) and the resulting crystalline Tafamidis polymorph is crystalline Tafamidis meglumine adduct (F). One possible adduct molecule can, for instance, be meglumine, which can be used in a 2:1 molar ration with respect to the Tafamidis. In the above described chemical surrounding it is possible to achieve high yields of crystalline meglumine adducts.

In another preferred embodiment of the process the Tafamidis acetic acid adduct (E) in step a) can be obtained by cyclization of 4-(3,5-dichlorobenzamido)-3-hydroxybenzoic acid (D) in the presence of acetic acid and a sulfonic acid

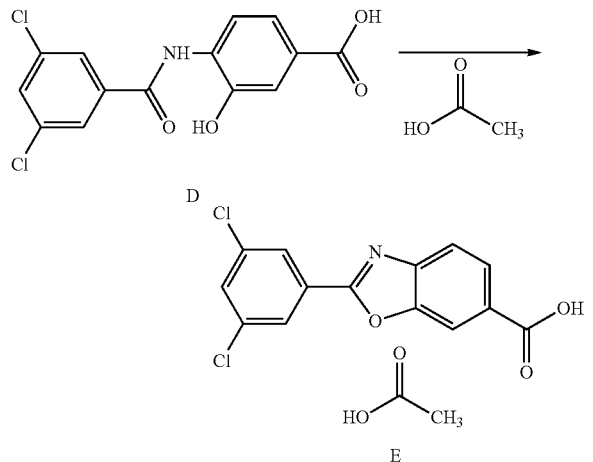

Surprisingly it was found that crystalline Tafamidis polymorphs could be reproducibly synthesized by a short and highly energy efficient route also reducing the probability of unwanted side-products. In addition, it is possible to perform the synthesis in safe and environmentally friendly solvents compared to state of the art processes. The overall yield in the single process steps are very good, and furthermore, gentle and high yield purification methods, especially for the intermediate D, are possible. It is very advantageous to proceed via the Tafamidis acetic acid adduct, because a low temperature process for processing and purification is obtained, achieving high purity levels at high overall yields. Therefore, the overall process delivers highly pure crystalline Tafamidis polymorphs at high yields in a less toxic and "greener" way compared to the state of the art processes.

The process may comprise a pre-step a), wherein 4-(3,5-dichlorobenzamido)-3-hydroxybenzoic acid (D) is reacted in order to form another ring structure at the educt (cyclization). The formed ring structure is an oxazole-ring and obtained via reaction of the benzamido- and the hydroxy-group of the educt. The cyclization reaction in the pre-step a) is performed in the presence of acetic acid. This means, that the reaction is either performed in a solution comprising acetic acid or in a solution consisting of acetic acid as solvent. It is further possible to use a mixture of acetic acid and pharmaceutically acceptable organic solvents or an aqueous acetic acid solution. It is preferred to perform the reaction in an aqueous/organic acetic acid solution comprising high acetic acid contents. The acetic acid content in the solvent may be higher than 30 weight-%, preferably higher than 75 weight-% and more preferred higher than 90 weight-%. Within these ratios a reproducible reaction at high yields is obtained.

Further, in the pre-step a) described above a sulfonic acid is used in order to perform the cyclization reaction. Suitable sulfonic acids can be selected from the group of methanesulfonic acid, benzensulfonic acid, toluenesulfonic acid, trifluoromethanesulfonic acid, xylene sulfonic acid or mixtures thereof. Preferred are sulfonic acids comprising at least one aromatic core. These acids are able to deliver high yields a short reaction times.

In another preferred embodiment the cyclization reaction pre-step a) can be performed in glacial acetic acid. It has been found very advantageous to perform the cyclization reaction in glacial acetic acid. Under these solvent conditions cyclization is achievable at short reaction times and low temperatures. In addition, the formation of the acetic acid adduct is accelerated resulting in overall low process times and a low amount of unwanted side-products. Without being bound to the theory it seems further advantageous to reduce the overall water content in this reaction step. Suitable water contents during cyclization may be lower than 25 weight-%, lower than 15 weight-% or even lower than 5 weight-%. These low water contents might help to reduce the amount of by-products and achieve high yields of the acetic acid adduct.

In another characteristic of the process the Tafamidis adduct interchange step b) from an acetic acid to a meglumine adduct can also be performed stepwise, wherein in a first step b1) the Tafamidis acetic acid adduct (E) is contacted with a solvent selected from the group consisting of aprotic apolar organic solvents followed by step b2), the adduct interchange in a solvent comprising water. Very high yields and short reaction times even at moderate temperatures could be obtained by using a two-step procedure for the adduct interchange reaction. This might be caused by the fact that firstly the acetic acid adduct is readily separated into Tafamidis and acetic acid in the apolar organic solvent, followed by adduct formation of an already fully dissolved meglumine. Suitable apolar organic solvents for dissolving of the acetic acid Tafamidis adduct can be selected from the group consisting of methyl-tertbutyl ether, diisoproyl ether, di-ethyl ether, ethylethanoate (EtOAc) or mixtures thereof. It has been found that theses solvents are able to readily dissolve the acetic acid adduct structure, without hindering the meglumine adduct formation. In addition, this group of solvents comprises low boiling points, easing afterwards the solvent removal.

Within a further preferred characteristic of the process the sulfonic acid in the cyclization reaction step a) can be p-toluenesulfonic acid. Especially, the use of p-toluenesulfonic acid has been shown to result in fast cyclization reactions comprising a very low amount of unwanted side-products. In addition, the acid does not interfere afterwards in the adduct formation/interchange reaction, therefore reducing the amount of cleaning operations.

In another aspect of the process the temperature in the steps a)-c) can be maintained below 125° C. In a further preferred embodiment of the process the overall temperatures and, especially, the temperatures in the drying step c) can be maintained above or equal to 5° C. and below or equal to 70° C. for a time period of longer or equal to 30 minutes and less or equal to 48 h to yield the crystalline Tafamidis polymorphs comprising a solvent content in the range of ≥0.0001 weight % and ≤5 weight %. It has been found very useful to strictly control the drying conditions in order to obtain storage stable material. Without being bound to the theory it is believed that the drying step in combination with the acetic acid adduct intermediate enables a very defined aligning of the other adducts to the Tafamidis, which in turn, favours the formation of the defined crystalline structure as described below. This process is further a function of the residual solvent content, wherein low solvent contents seem to accelerate the formation of the crystalline structures. This finding is different to the state of the art processes, wherein the solvent content of Tafamidis compounds seems rather high.

It is within the scope of invention to further disclose a crystalline Tafamidis free acid polymorph, wherein the crystalline form comprises peaks at diffraction angles of 5.1, 14.1, and 18.5 (2θ±0.2 respectively) in a powder X-ray diffraction pattern. It is possible to obtain a crystalline form of the Tafamidis free acid by the inventive process. This form is especially obtainable by an adduct interchange starting from the Tafamidis acetic acid adduct in the presence of a water/ethyl acetate solvent as described above. This route enables large scale processing and delivers high yields of very pure Tafamidis free acid.

It is within the scope of invention to further disclose a crystalline Tafamidis acetic acid adduct, characterized in that said crystalline form comprises peaks at diffraction angles of 12.2, 23.0 and 25.5 (2θ±0.2 respectively) in a powder X-ray diffraction pattern. The Tafamidis acetic acid adduct can be synthesized according to the above described pre-step and according to the further processing in the steps b and c). High yields of crystalline material is obtainable via such route.

It is within the scope of invention to further disclose a Crystalline Tafamidis formic acid adduct, wherein the crystalline form comprises peaks at diffraction angles of 5.0, 10.0, and 20.1 (2θ±0.2 respectively) in a powder X-ray diffraction pattern. In addition, also a formic acid polymorph can be obtained via the acetic acid adduct interchange. The formic acid polymorph shows a high crystallinity and high yields are obtainable via such route. This polymorph can for instance be obtained by performing the process using formic acid as solvent.

It is within the scope of invention to further disclose a crystalline Tafamidis meglumine (F), characterized in that said crystalline form comprises peaks at diffraction angles of 12.2, 23.0 and 25.5 (2θ±0.2 respectively) in a powder X-ray diffraction pattern. Within step a) also an adduct interchange can be performed in the presence of N-methyl-D-glucamine. This means that within this step the interactions between acetic acid and Tafamidis is broken and replaced by an interaction of Tafamidis and meglumine. This process step can be a two-step process, wherein breaking of the first adduct is separated from generating the Tafamidis meglumine adduct or it is also possible to perform this adduct interchange in a one-step reaction. At the end a Tafamidis meglumine adduct can be achieved, wherein one N-methyl-D-glucamine is interacting with one Tafamidis molecule.

The meglumine adduct may for instance be achieved by adding meglumine to the dispersion obtained in step a). It is found that this Tafamidis meglumine polymorph is very stable and is especially insensitive to pressure treatments compared to the known solid state forms of Tafamidis meglumine. Such processing profile renders this Tafamidis meglumine polymorph particularly suitable for the preparation of solid pharmaceutical compositions for oral administration, because the polymorph remains unchanged even at harsh tableting conditions.

In another aspect the crystalline Tafamidis meglumine may comprise peaks at diffraction angles of 5.5, 12.2, 17.2, 24.7, 23.0 and 25.5 (2θ±0.2 respectively) in a powder X-ray diffraction pattern. In addition to the definition of this new Tafamidis meglumine polymorph by using 3 characteristic peak positions it is also possible to further define the same polymorph by using 6 characteristic peak positions. The polymorphic form exhibiting such diffraction pattern reveals good processing characteristic such as a good compactability, high solubility and low hygroscopicity. Therefore, this Tafamidis meglumine polymorph is very suitable for pharmaceutical processing. A suitable description of the new polymorph can also be presented by 5.5, 12.2, 17.2 and 24.7 (2θ±0.2 respectively) or by 5.5, 12.2, 17.2, 24.7 and 23.0 (2θ±0.2 respectively).

It is further within the scope of the invention to disclose a new intermediate in the production of Tafamidis meglumine, wherein the intermediate is a Tafamidis acetic acid adduct. It has been found that the Tafamidis acetic acid route comprising the Tafamidis acetic acid adduct or acetic acid solvate is a very straight, reproducible and high yield route in order to obtain Tafamidis meglumine in a crystalline solid form. In addition, the intermediate is easy to purify and very storage stable compared to other intermediates proposed in the prior art. For other advantages of the intermediate it is referred to the advantages disclosed in the description of the inventive process.

Furthermore, also a pharmaceutical composition comprising the above described crystalline Tafamidis adducts is within the scope of the invention. These pharmaceutical compositions comprise for instance at least the inventive Tafamidis meglumine polymorph as an API (Active Pharmaceutical Ingredient) and optionally further pharmaceutical acceptable excipients. The inventively achievable Tafamidis meglumine polymorph is especially suitable for use in a pharmaceutical composition because the polymorph can be processed in a more reproducible way compared to other Tafamidis meglumine forms. Hence, pharmaceutical compositions are accessible comprising an improved shelf life and more homogeneous characteristics.

In a preferred embodiment the pharmaceutical composition can be an oral dosage form. Especially the inventive Tafamidis meglumine polymorph is suitable for being processed into oral dosage forms. This suitability can especially be based on the pressure insensitivity, chemical stability and compressibility of this special polymorph. Therefore, the inventive polymorph is easily processable even in harsh tableting steps and comprises a very good storage stability.

In addition, the use of above described pharmaceutical compositions for the treatment of familial amyloid polyneuropathy (FAP), familial transthyretin (TTR) amyloidosis or transthyretin (TTR) familial amyloid polyneuropathy (FAP) is according to the invention.

BRIEF DESCRIPTION OF THE DRAWINGS

The invention at hand is further exemplified in certain embodiments, wherein the FIGS. 1 to 17 show.

DETAILED DESCRIPTION

Figure 1:
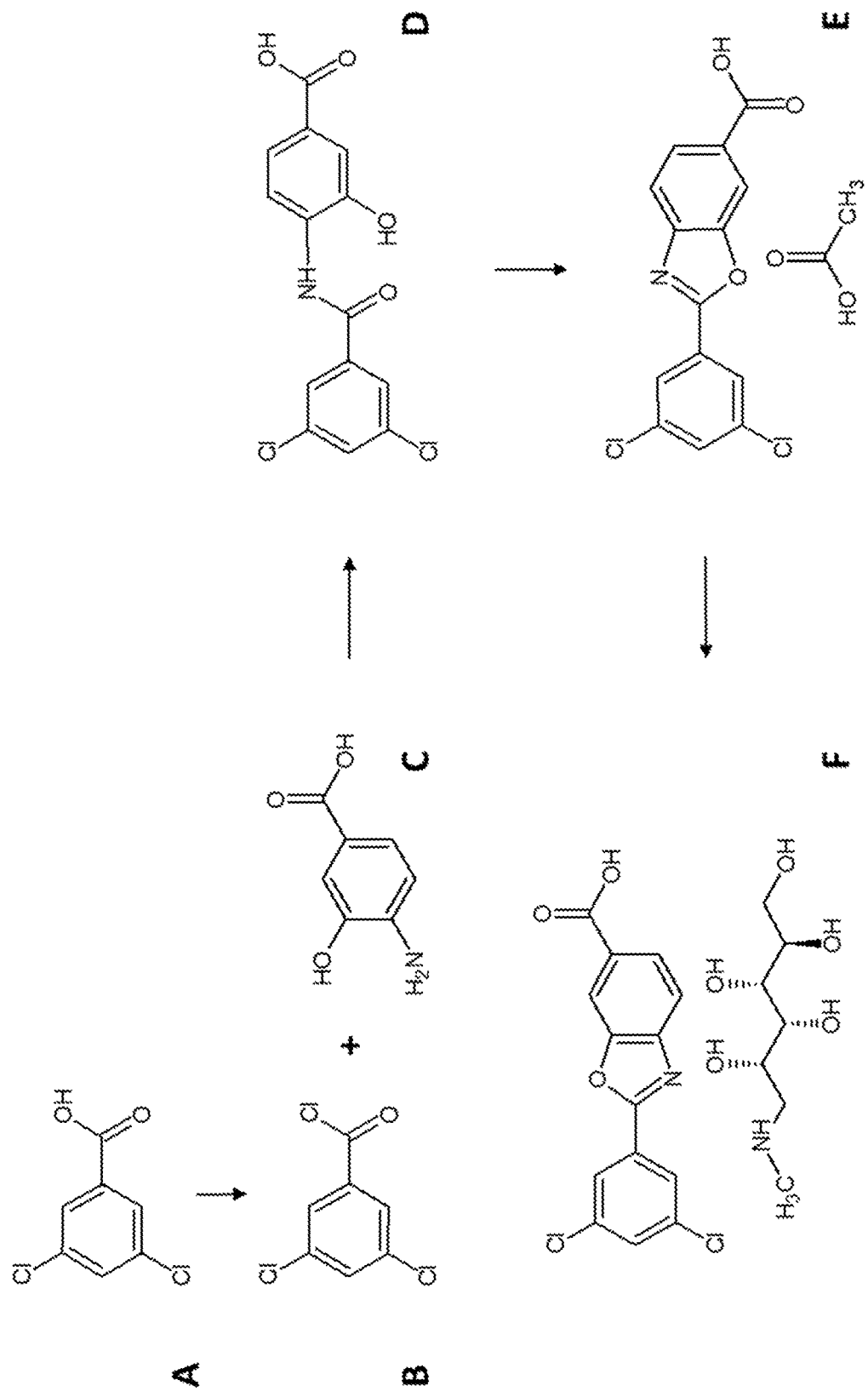
FIG. 1 one possible route of synthesis for obtaining crystalline Tafamidis meglumine.

FIG. 1 displays a possible route of synthesis for obtaining Tafamidis meglumine. In a pre-step 3,5-dichlorobenzoic acid (A) may be functionalized in order to obtain the chloro-functionalized 3,5-dichlorobenzoyl chloride. This step is optional and the following route of synthesis may also start for the already functionalized molecule as educt. In a first reaction step the functionalized benzoyl-chloride is reacted with 4-amino-3-hydroxybenzoic acid (C) to yield 4-[(3,5-dichlorobenzoyl) amino]-3-hydroxy-benzoic acid (D). The reaction can be performed in THF. The intermediate (D) is further processed by cyclization in the presence of acetic and a sulfonic acid derivative to yield the Tafamidis acetic acid adduct (E), wherein the latter is the starting educt for obtaining another crystalline Tafamidis polymorphs. The acetic acid adduct may further be treated by an adduct exchange step to yield the Tafamidis meglumine adduct (F).

Figure 2:
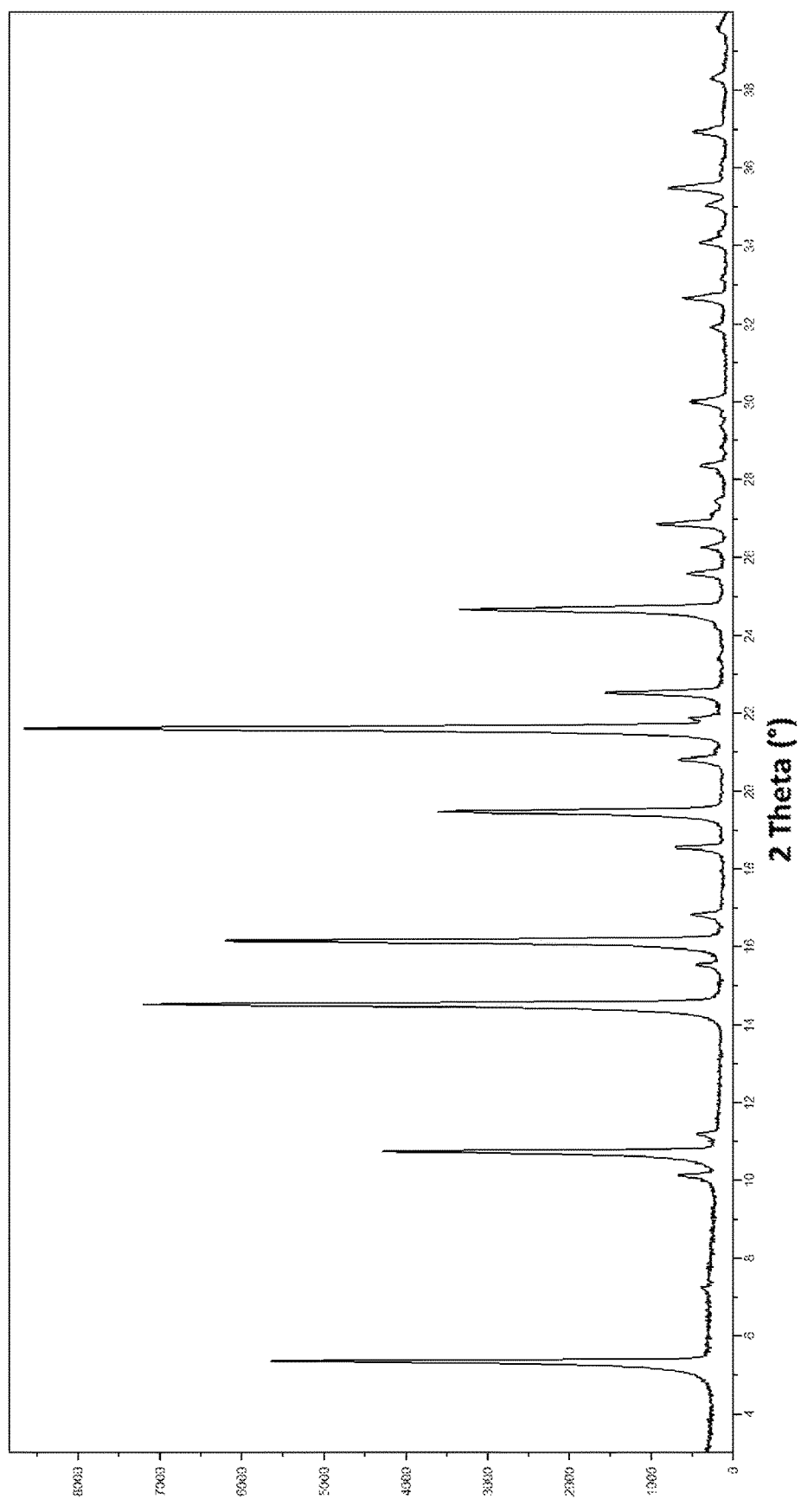
FIG. 2 a PXRD diffraction pattern of intermediate E, the Tafamidis acetic acid adduct.

FIG. 2 shows a PXRD diffraction pattern of intermediate E, the Tafamidis acetic acid adduct. The experimental setup for assessing the diffraction pattern is described further below in the experimental section. The diffraction pattern of the acetic acid adduct comprise the following intensity distribution

| °/2 θ | d-spacing/Å | Intensity (rel.) |
|---|---|---|
| 5.3 | 16.52 | 61 |
| 7.2 | 12.27 | 1 |
| 10.1 | 8.76 | 5 |
| 10.7 | 8.24 | 47 |
| 11.2 | 7.92 | 3 |
| 14.5 | 6.10 | 82 |
| 15.4 | 5.71 | 3 |
| 16.2 | 5.49 | 71 |
| 16.8 | 5.27 | 4 |
| 18.6 | 4.78 | 7 |
| 19.5 | 4.56 | 10 |
| 20.8 | 4.27 | 6 |
| 21.6 | 4.11 | 100 |
| 22.5 | 3.95 | 16 |
| 24.7 | 3.61 | 37 |
| 25.6 | 3.48 | 5 |
| 26.3 | 3.39 | 3 |
| 26.9 | 3.32 | 10 |
| 27.1 | 3.29 | 2 |
| 27.5 | 3.25 | 1 |
| 28.3 | 3.15 | 4 |
| 30.0 | 2.98 | 5 |
| 31.9 | 2.81 | 2 |
| 32.7 | 2.74 | 6 |
| 34.1 | 2.63 | 4 |
| 35.0 | 2.56 | 3 |
| 35.5 | 2.53 | 8 |
| 36.9 | 2.44 | 5 |
| 38.3 | 2.35 | 2 |
| 39.5 | 2.28 | 1 |

It can be deduced from the diffraction pattern that the acetic acid adduct obtained according to the invention is comprises a crystalline structure and is a distinct Tafimidis actetic acid polymorph.

Figure 3:
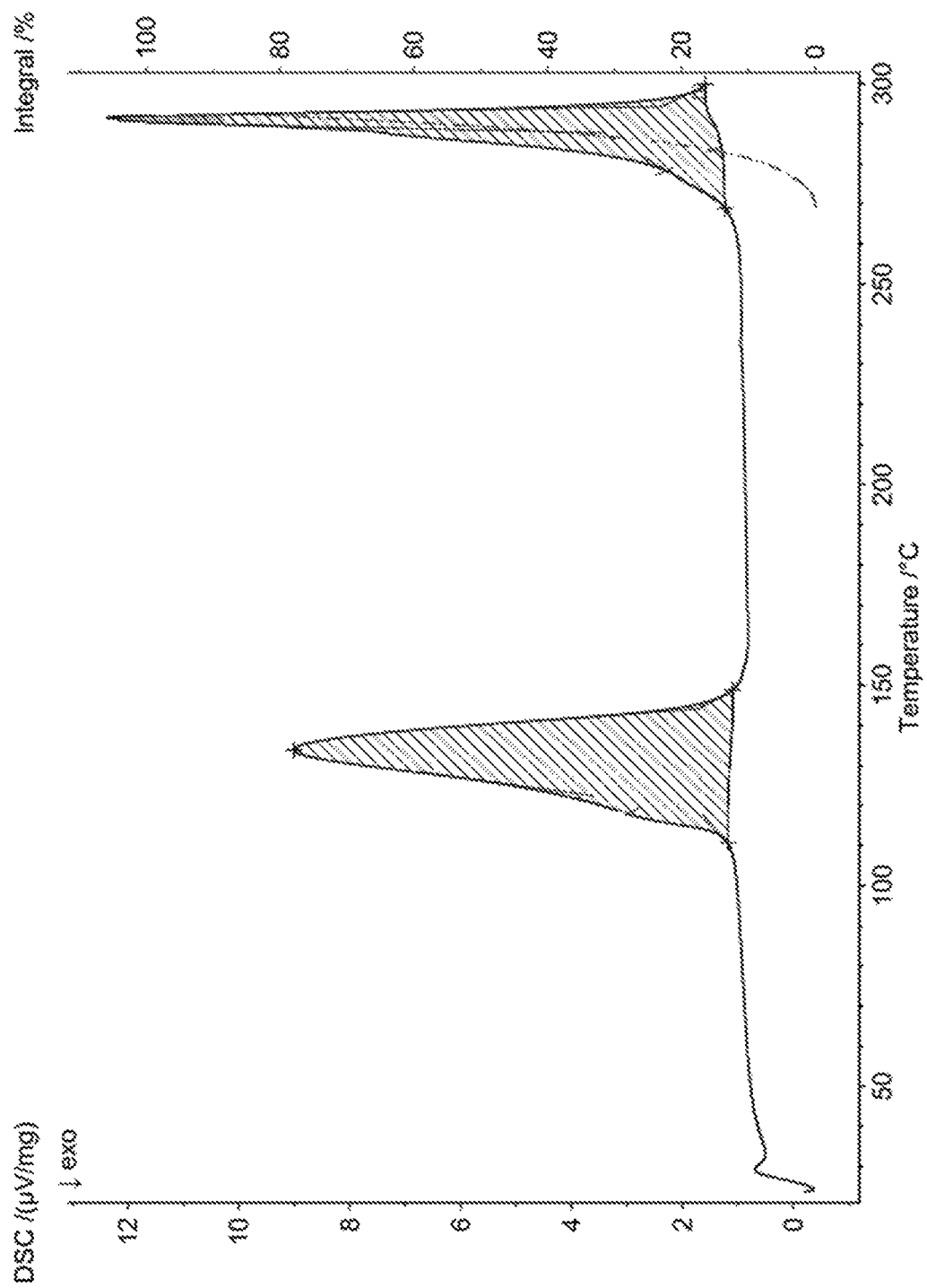
FIG. 3 a DSC-Thermogram of intermediate E, the Tafamidis acetic acid adduct.

FIG. 3 exhibits the DSC-curve of the Tafamidis acetic acid adduct. The experimental setup for assessing the DSC-thermogram is described further below in the experimental section. The product is obtained via the inventive route of synthesis and displays an endothermic peak at around 134° C. (peak maximum) and a further endothermic peak at approximately 292° C.

Figure 4:
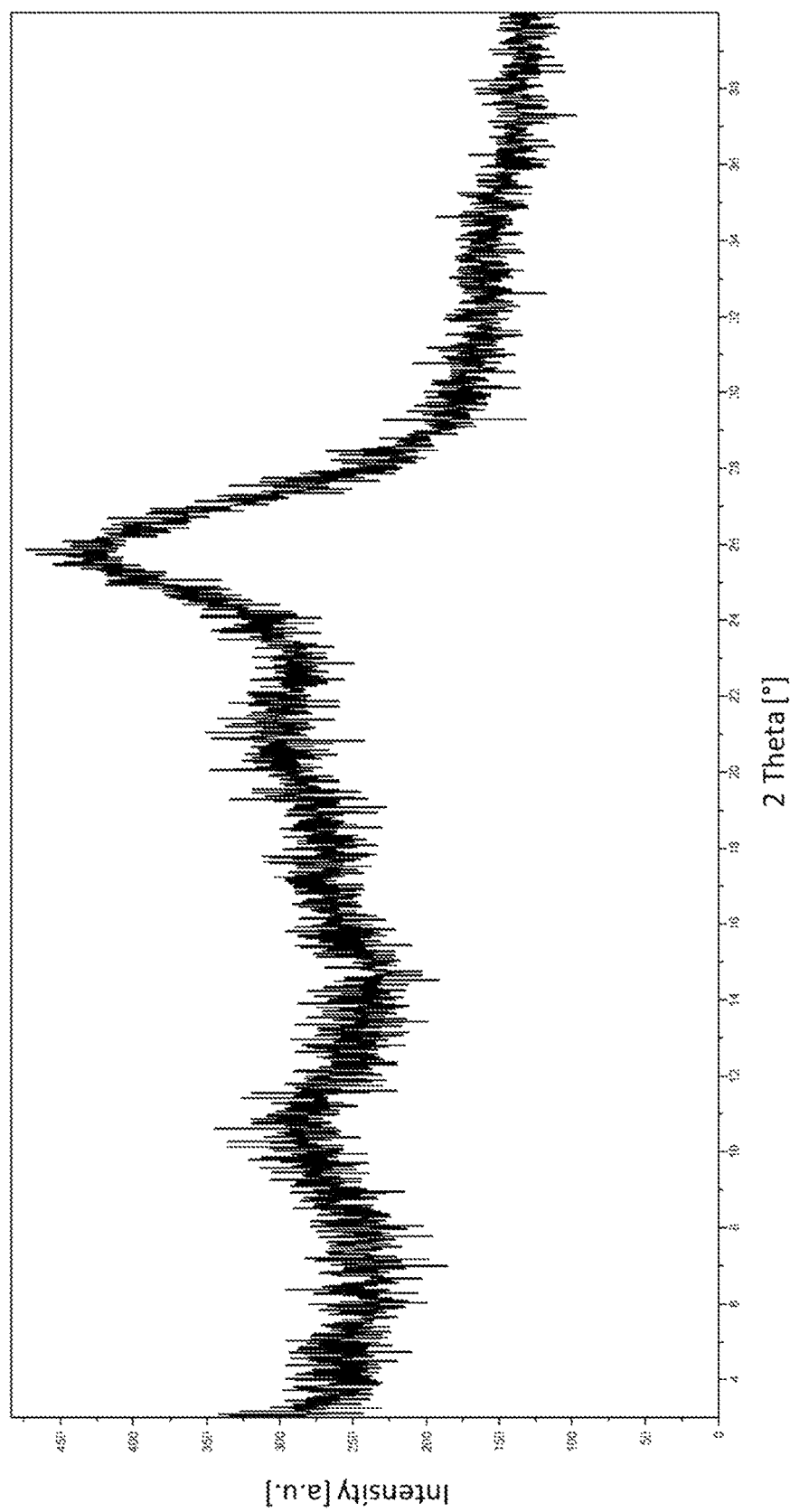
FIG. 4 a PXRD diffraction pattern of amorphous Tafamidis meglumine synthesized not according to the invention.

FIG. 4 displays the PXRD diffraction pattern of dry amorphous Tafamidis meglumine. The Tafamidis meglumine is essentially amorphous, comprising only two rather broad halos around 10° and 26 (20), respectively.

Figure 5:
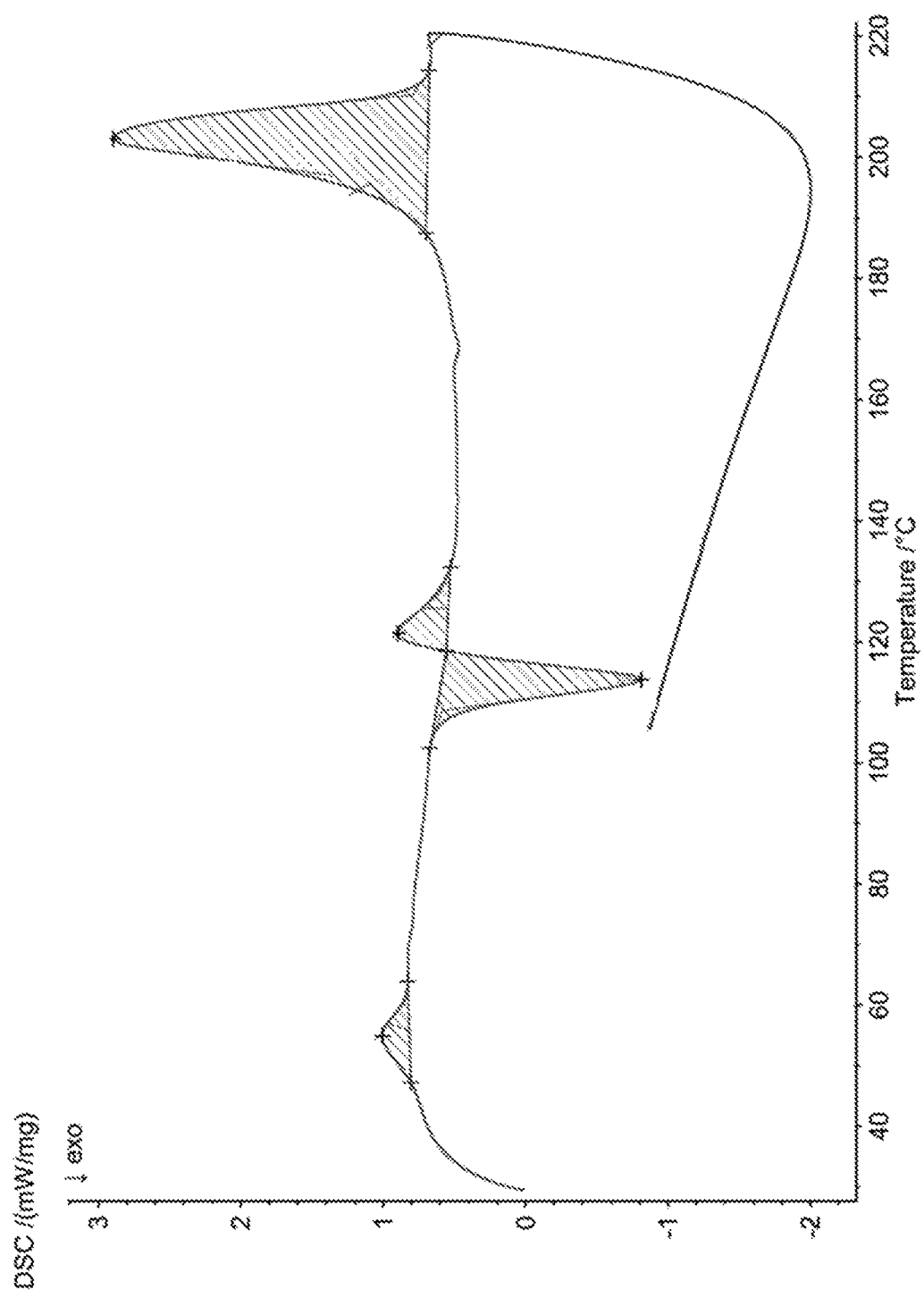
FIG. 5 a DSC-Thermogram of amorphous Tafamidis meglumine synthesized not according to the invention.

FIG. 5 show the DSC-curve of amorphous Tafamidis meglumine. The material was prepared according to method 2 described below. The DSC reveals a small endothermic peak around 55° C., an exothermic peak at 114° C. followed by an endothermic peak around 122° C. followed by melting of the amorphous material around 203° C.

Figure 6:
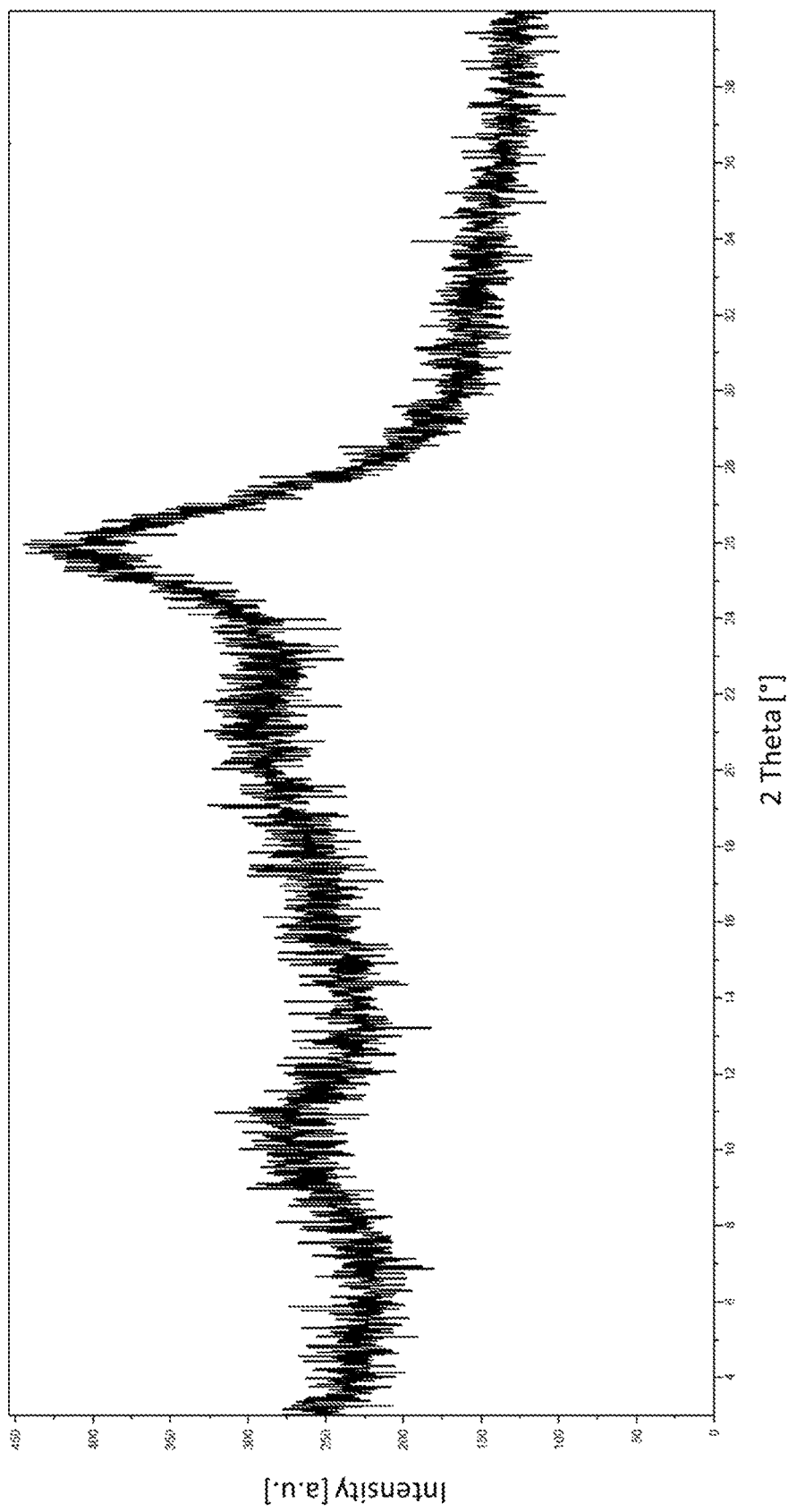
FIG. 6 a PXRD diffraction pattern of amorphous Tafamidis meglumine synthesized not according to the invention and additionally dried.

FIG. 6 reveals the PXRD diffraction pattern of amorphous Tafamidis meglumine. This sample was additionally dried overnight in a vacuum oven. The sample is essentially amorphous comprising no distinct diffraction peaks. Instead rather broad halos around 10° and 22° are visible. In addition, a broad but distinct peak is visible around 27° (all values 20).

Figure 7:
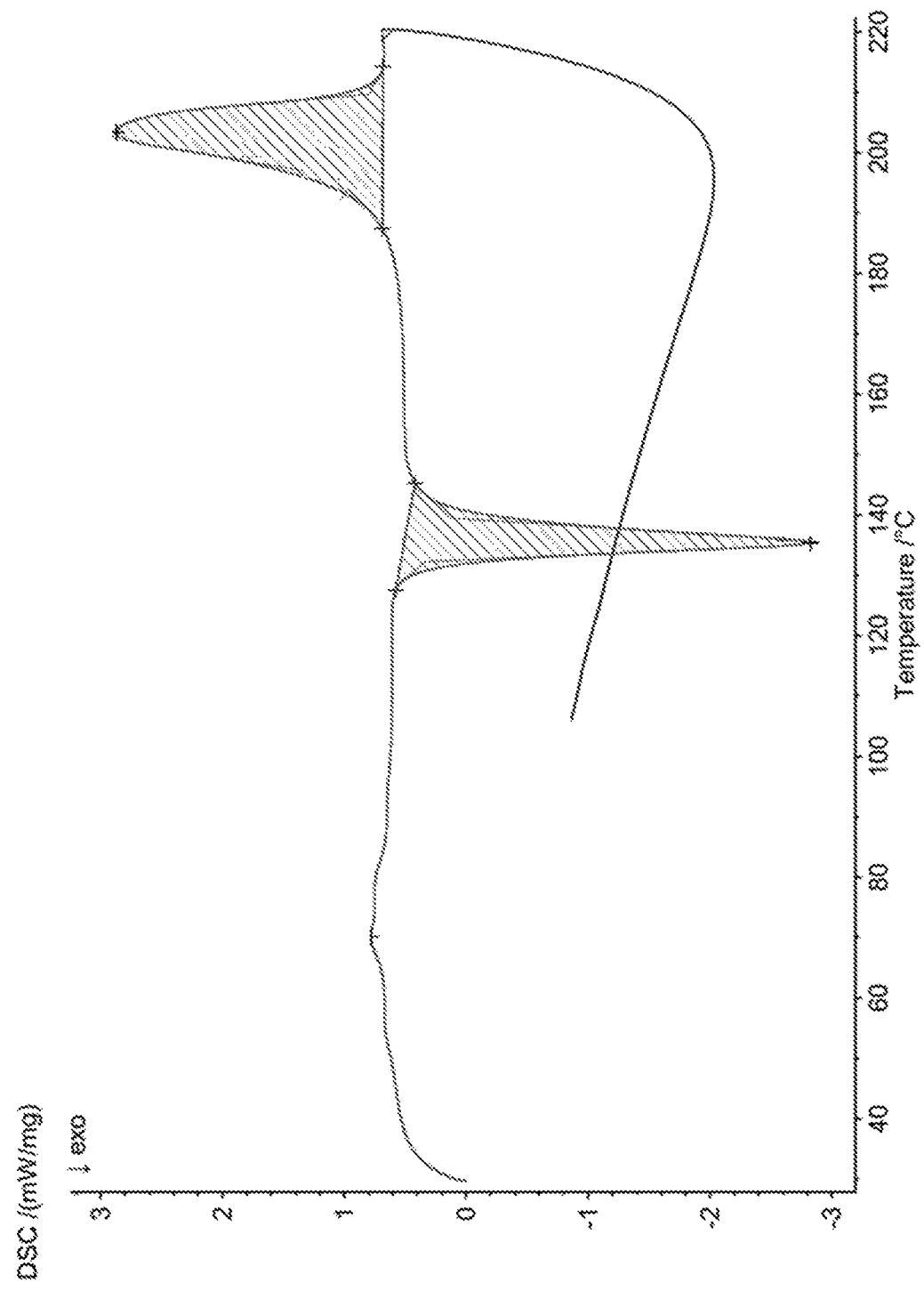
FIG. 7 a DSC-Thermogram of amorphous Tafamidis meglumine synthesized not according to the invention and additionally dried.

FIG. 7 shows the DSC-curve of the amorphous Tafamidis meglumine. This sample was additionally dried overnight in a vacuum oven. The sample comprises an exothermic peak around 135° C. (max) and an endothermic melting around 203° C. It appeared, that the overall phase transition temperature is also a function of the water content, wherein lower water contents shift the phase transition to higher temperatures. The melting temperature of the amorphous material is nearly not affected by the additional drying step.

Figure 8:
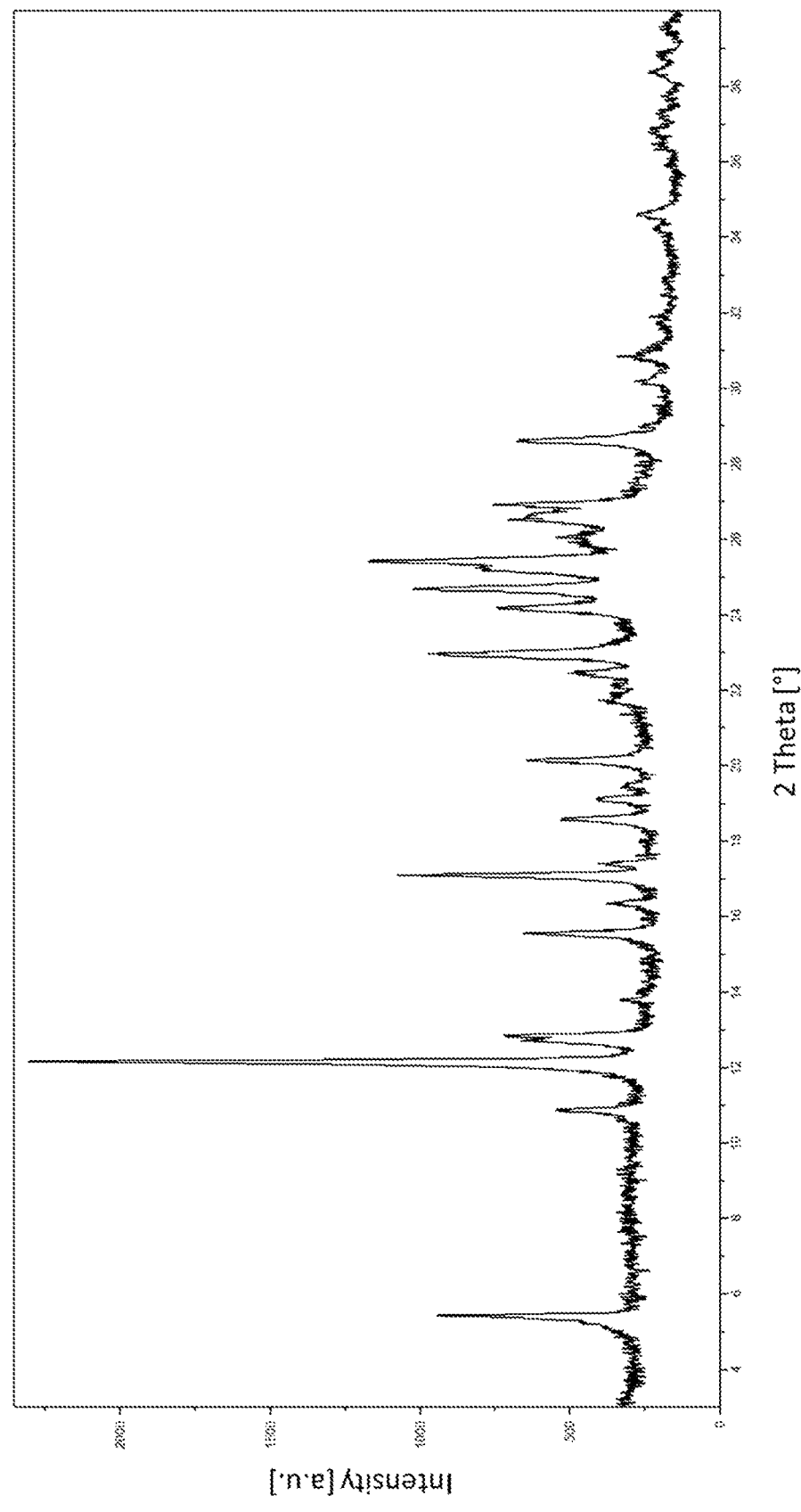
FIG. 8 a PXRD diffraction pattern of the crystalline Tafamidis meglumine polymorph processed by thermal annealing.

FIG. 8 displays the PXRD diffraction pattern of crystalline Tafamidis meglumine obtained not according to the invention via melting of amorphous Tafamidis meglumine at higher temperatures. The material was obtained according to the annealing route as described below. The diffraction pattern exhibits peak positions at:

| °/2 θ | d-spacing/Å | Intensity (rel.) |
|---|---|---|
| 5.4 | 16.28 | 33 |
| 10.9 | 8.14 | 13 |
| 12.2 | 7.28 | 100 |
| 12.8 | 6.92 | 20 |
| 13.8 | 6.41 | 3 |
| 15.6 | 5.70 | 21 |
| 16.3 | 5.42 | 7 |
| 17.1 | 5.19 | 40 |
| 17.4 | 5.10 | 8 |
| 18.6 | 4.77 | 15 |
| 19.1 | 4.65 | 8 |
| 19.5 | 4.56 | 4 |
| 20.1 | 4.41 | 20 |
| 21.7 | 4.10 | 6 |
| 22.5 | 3.96 | 10 |
| 22.9 | 3.88 | 33 |
| 24.2 | 3.68 | 22 |
| 24.7 | 3.61 | 34 |
| 25.2 | 3.54 | 23 |
| 25.4 | 3.50 | 43 |
| 26.1 | 3.42 | 11 |
| 26.5 | 3.36 | 19 |
| 26.9 | 3.31 | 22 |
| 28.6 | 3.12 | 23 |
| 30.2 | 2.96 | 4 |
| 30.8 | 2.90 | 6 |
| 34.2 | 2.62 | 3 |
| 34.6 | 2.59 | 7 |
| 36.4 | 2.47 | 3 |
| 36.8 | 2.44 | 4 |
| 37.2 | 2.41 | 3 |
| 37.7 | 2.39 | 2 |
| 38.4 | 2.35 | 4 |
| 38.8 | 2.32 | 3 |

The diffraction pattern of this crystalline material is distinctively different compared to the crystalline diffraction pattern of the acetic acid adduct material. The crystalline material can especially be characterized by the following groups of diffraction peaks, 5.4, 12.2, 17.1, 22.9, 24.7, 26.9, 28.6 or 5.4, 12.2, 17.1, 22.9, 24.7 or 5.4, 12.2, 17.1, 22.9 (2θ±0.2 respectively).

Figure 9:
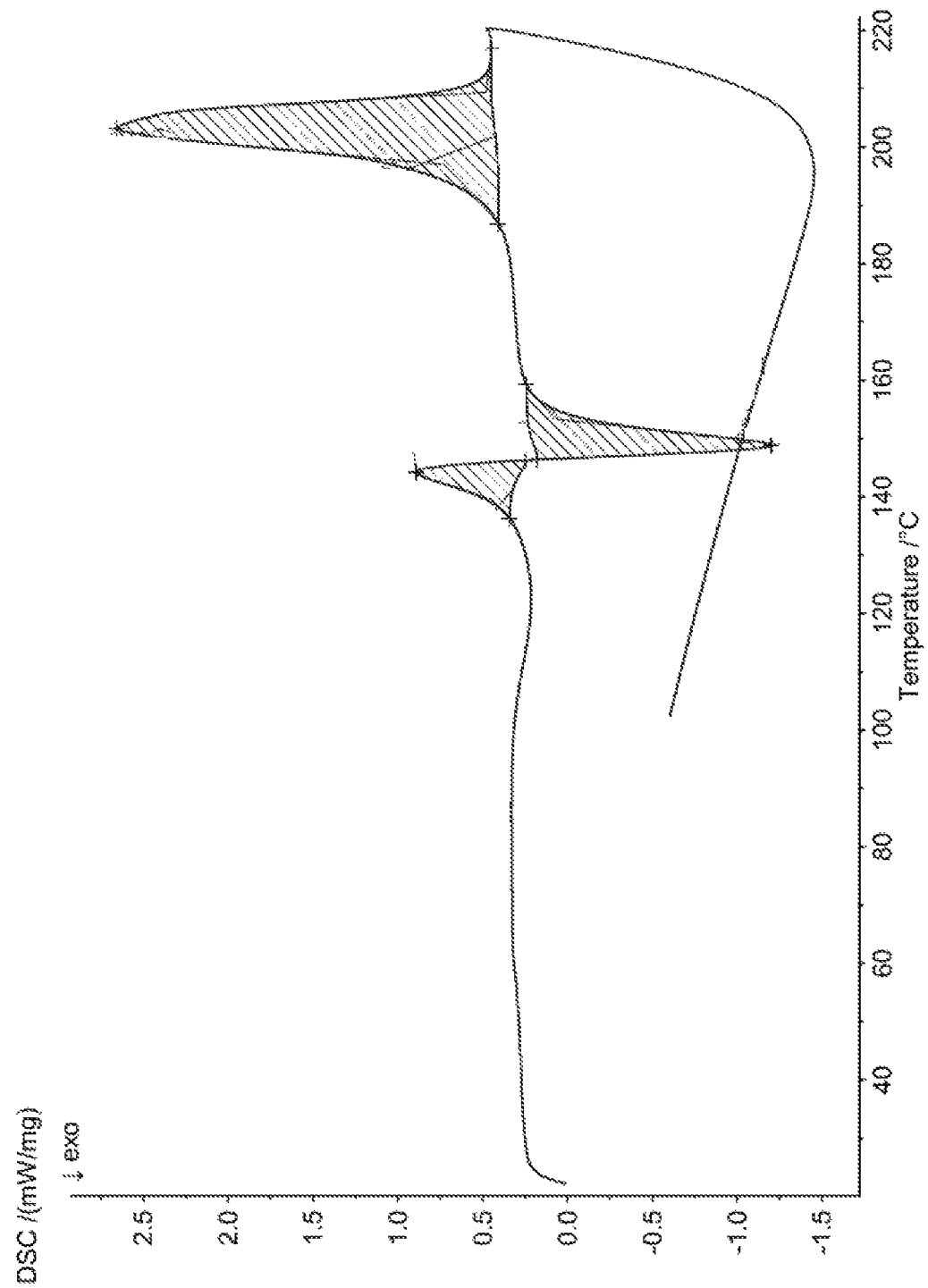
FIG. 9 a DSC-Thermogram of the inventive crystalline Tafamidis meglumine polymorph processed by thermal annealing.

FIG. 9 displays the DSC-curve of crystalline Tafamidis meglumine obtained via melting of amorphous Tafamidis meglumine at higher temperatures. The material was obtained according to the annealing route as described below. The DSC comprises an endothermic peak at 144° C., immediately followed by an exothermic peak at 149° C. The material also melts at 203° C.

Figure 10:
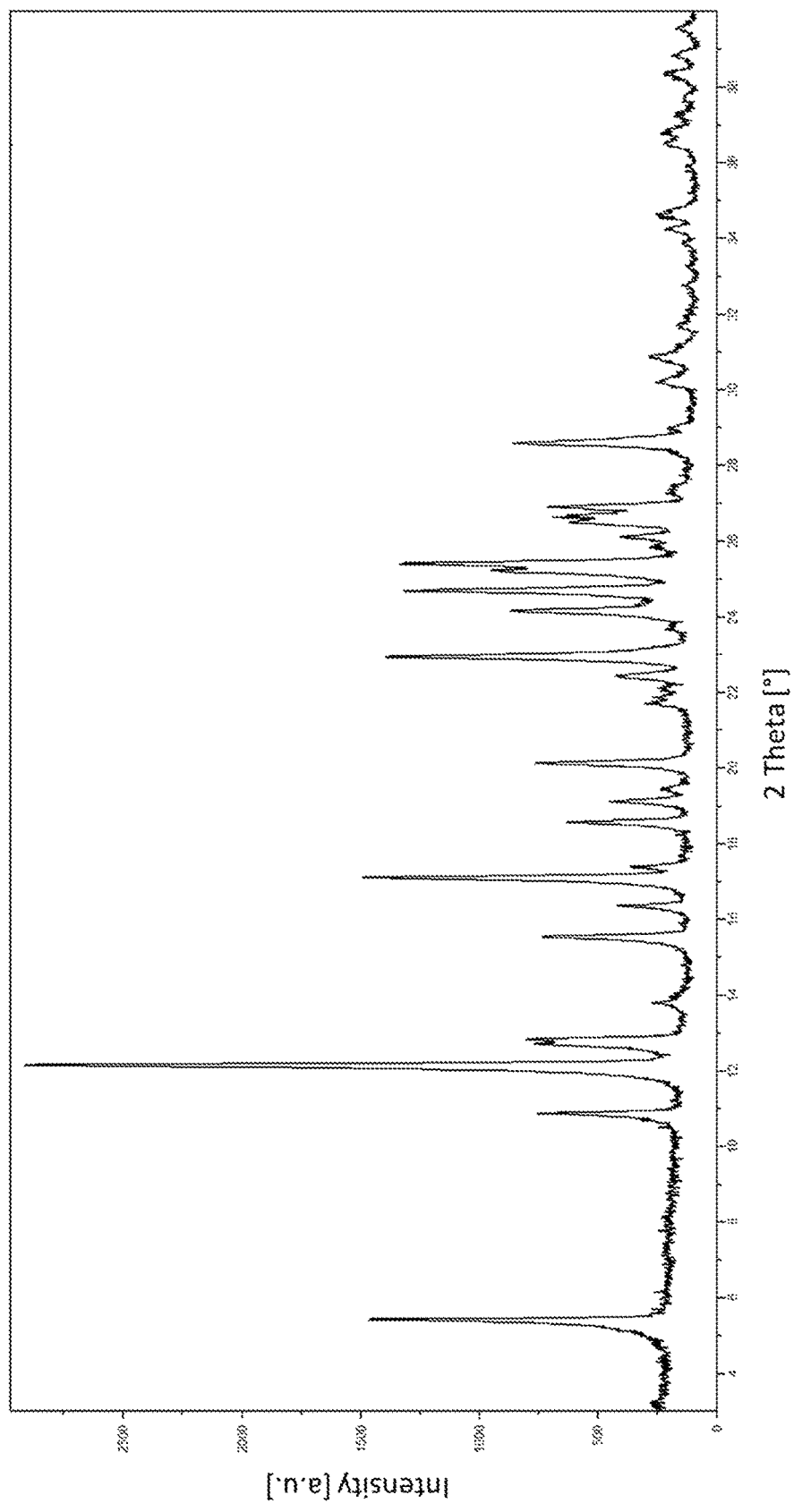
FIG. 10 a PXRD diffraction pattern of crystalline Tafamidis meglumine polymorph processed by processed by dispersion/evaporation in pentane/hexane.

FIG. 10 shows the PXRD diffraction pattern of the inventive crystalline Tafamidis meglumine polymorph processed by dispersion/evaporation in pentane/heptane as described below. The obtained crystalline form is within the limits of experiments the same as obtained by the vacuum method. The PXRD reveals diffraction peaks at

| °/2 θ | d-spacing/Å | Intensity (rel.) |
|---|---|---|
| 5.4 | 16.27 | 46 |
| 10.9 | 8.13 | 21 |
| 12.2 | 7.28 | 100 |
| 12.7 | 6.97 | 22 |
| 12.8 | 6.89 | 21 |
| 13.8 | 6.43 | 4 |
| 15.5 | 5.70 | 22 |
| 16.4 | 5.42 | 10 |
| 17.1 | 5.18 | 49 |
| 17.4 | 5.10 | 8 |
| 18.6 | 4.78 | 18 |
| 19.1 | 4.64 | 11 |
| 19.4 | 4.57 | 3 |
| 20.1 | 4.41 | 23 |
| 21.7 | 4.10 | 5 |
| 22.1 | 4.02 | 3 |
| 22.4 | 3.97 | 9 |
| 22.9 | 3.88 | 45 |
| 24.1 | 3.69 | 26 |
| 24.7 | 3.61 | 42 |
| 25.2 | 3.54 | 26 |
| 25.4 | 3.51 | 42 |
| 25.8 | 3.45 | 3 |
| 26.1 | 3.41 | 9 |
| 26.5 | 3.37 | 17 |
| 26.6 | 3.35 | 17 |
| 26.9 | 3.32 | 20 |
| 27.5 | 3.25 | 2 |
| 28.6 | 3.12 | 27 |
| 29.0 | 3.08 | 3 |
| 30.2 | 2.96 | 5 |
| 30.9 | 2.90 | 6 |
| 31.7 | 2.83 | 2 |
| 32.8 | 2.73 | 1 |
| 33.2 | 2.70 | 1 |
| 34.2 | 2.62 | 5 |
| 34.6 | 2.59 | 6 |
| 36.5 | 2.46 | 4 |
| 36.8 | 2.44 | 4 |
| 37.2 | 2.42 | 2 |
| 37.7 | 2.38 | 1 |
| 38.3 | 2.35 | 4 |
| 38.8 | 2.32 | 3 |
| 39.6 | 2.28 | 2 |

Within the experimental error the spectrum is identical to the PXRD diffraction pattern of the crystalline material obtained by melting at higher temperatures, indicating that the same polymorph was obtained by the different processing routes, i.e. dispersion/evaporation vs. melting at elevated temperatures.

Figure 11:
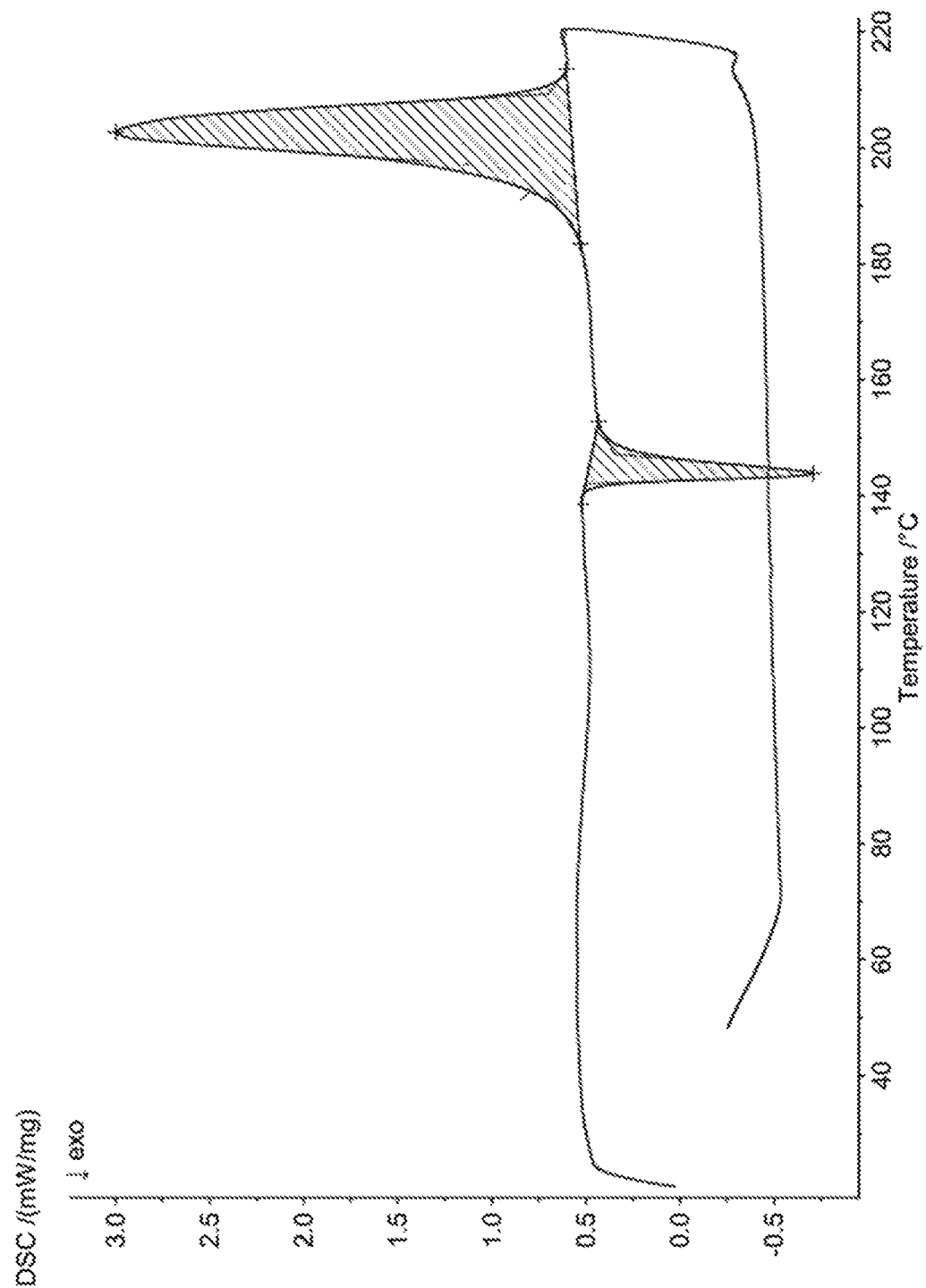
FIG. 11 a DSC-Thermogram of the crystalline Tafamidis meglumine polymorph processed by processed by dispersion/evaporation in pentane/hexane.

FIG. 11 reveals the DSC-curve of the inventive crystalline Tafamidis meglumine polymorph processed by dispersion/evaporation in pentane/heptane as described below. The DSC reveals that the obtained crystalline form comprises an exothermic transition around 145° C. followed by melting at 201'C. Especially, the exothermic and the melting transitions are very similar in temperature compared to the crystalline material processed by melting at higher temperatures.

Figure 12:
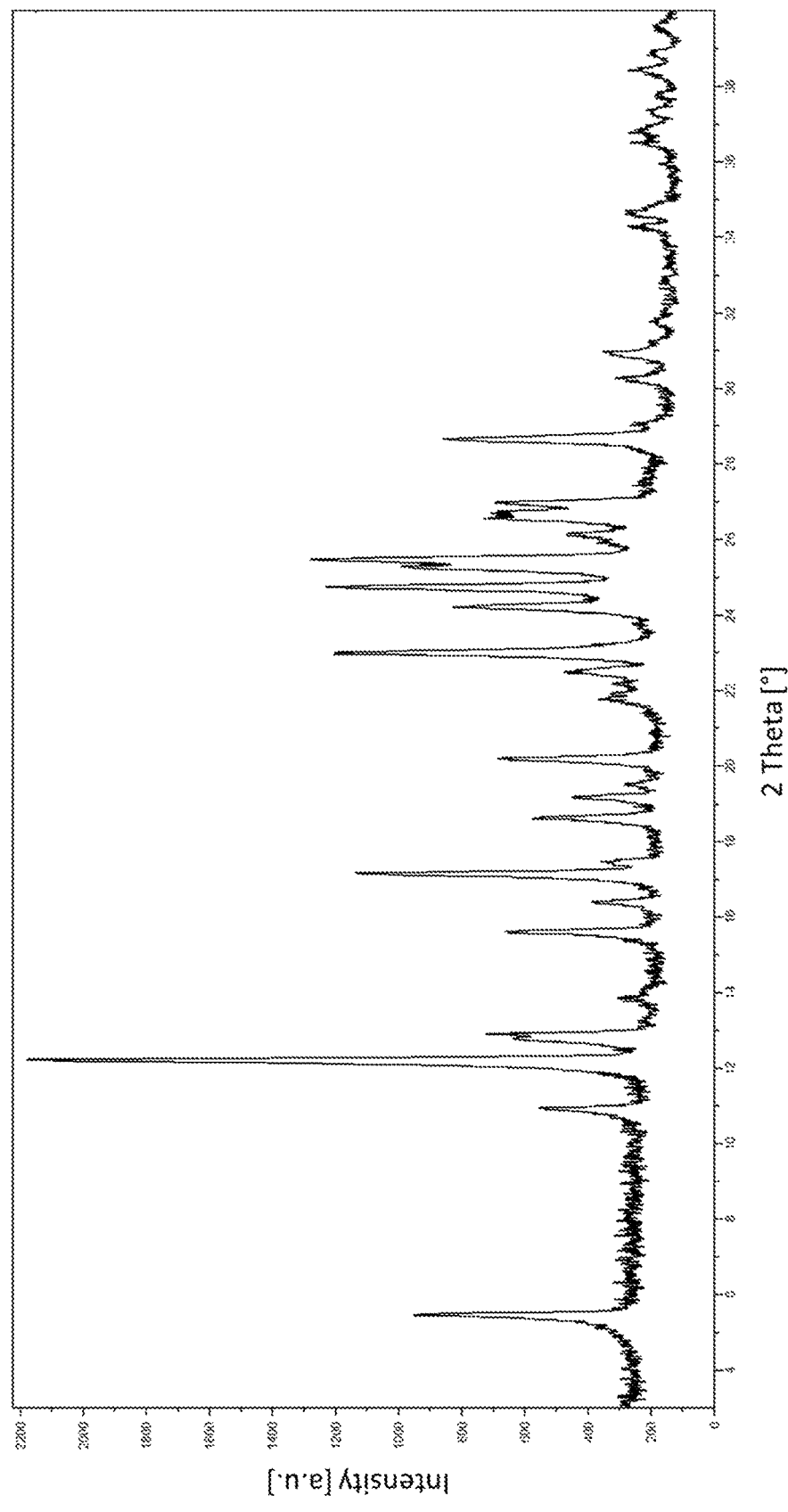
FIG. 12 a PXRD diffraction pattern of the inventive crystalline Tafamidis meglumine polymorph processed by thermal treatment of amorphous Tafamidis meglumine.

FIG. 12 displays the PXRD diffraction pattern of the crystalline Tafamidis meglumine polymorph processed by dispersion/evaporation in pentane/hexane. The obtained crystalline form is within the limits of experiments the same as obtained by the vacuum method. The PXRD reveals diffraction peaks at

| °/2 θ | d-spacing/Å | Intensity (rel.) |
|---|---|---|
| 5.5 | 16.13 | 36 |
| 10.9 | 8.09 | 17 |
| 12.2 | 7.24 | 100 |

-continued

| °/2 θ | d-spacing/Å | Intensity (rel.) |
|---|---|---|
| 12.8 | 6.94 | 22 |
| 12.9 | 6.85 | 25 |
| 13.9 | 6.39 | 5 |
| 15.6 | 5.67 | 23 |
| 16.4 | 5.41 | 9 |
| 17.2 | 5.16 | 51 |
| 17.5 | 5.07 | 8 |
| 18.7 | 4.76 | 20 |
| 19.2 | 4.63 | 14 |
| 19.5 | 4.55 | 5 |
| 20.2 | 4.40 | 26 |
| 21.0 | 4.23 | 22 |
| 21.8 | 4.08 | 7 |
| 21.0 | 4.05 | 6 |
| 22.2 | 4.01 | 6 |
| 22.5 | 3.95 | 13 |
| 23.0 | 3.86 | 52 |
| 24.2 | 3.68 | 33 |
| 24.7 | 3.60 | 50 |
| 25.2 | 3.53 | 39 |
| 25.5 | 3.50 | 55 |
| 26.1 | 3.41 | 12 |
| 26.5 | 3.36 | 27 |
| 26.7 | 3.34 | 24 |
| 27.0 | 3.31 | 25 |
| 28.7 | 3.12 | 37 |
| 29.1 | 3.07 | 3 |
| 30.3 | 2.95 | 7 |
| 30.9 | 2.89 | 10 |
| 31.8 | 2.82 | 2 |
| 34.3 | 2.62 | 6 |
| 34.6 | 2.59 | 7 |
| 36.5 | 2.46 | 4 |
| 36.8 | 2.44 | 5 |
| 37.3 | 2.41 | 3 |
| 37.8 | 2.38 | 2 |
| 38.4 | 2.34 | 6 |
| 28.9 | 2.32 | 4 |

Within the accuracy of the method the position of the diffraction peaks is the same compared to the positions of the diffraction peaks for the crystalline material obtained either by the melting at elevated temperatures or by dispersion/evaporation in pentane/heptane, indicating the formation of the same polymorphic structure.

Figure 13:
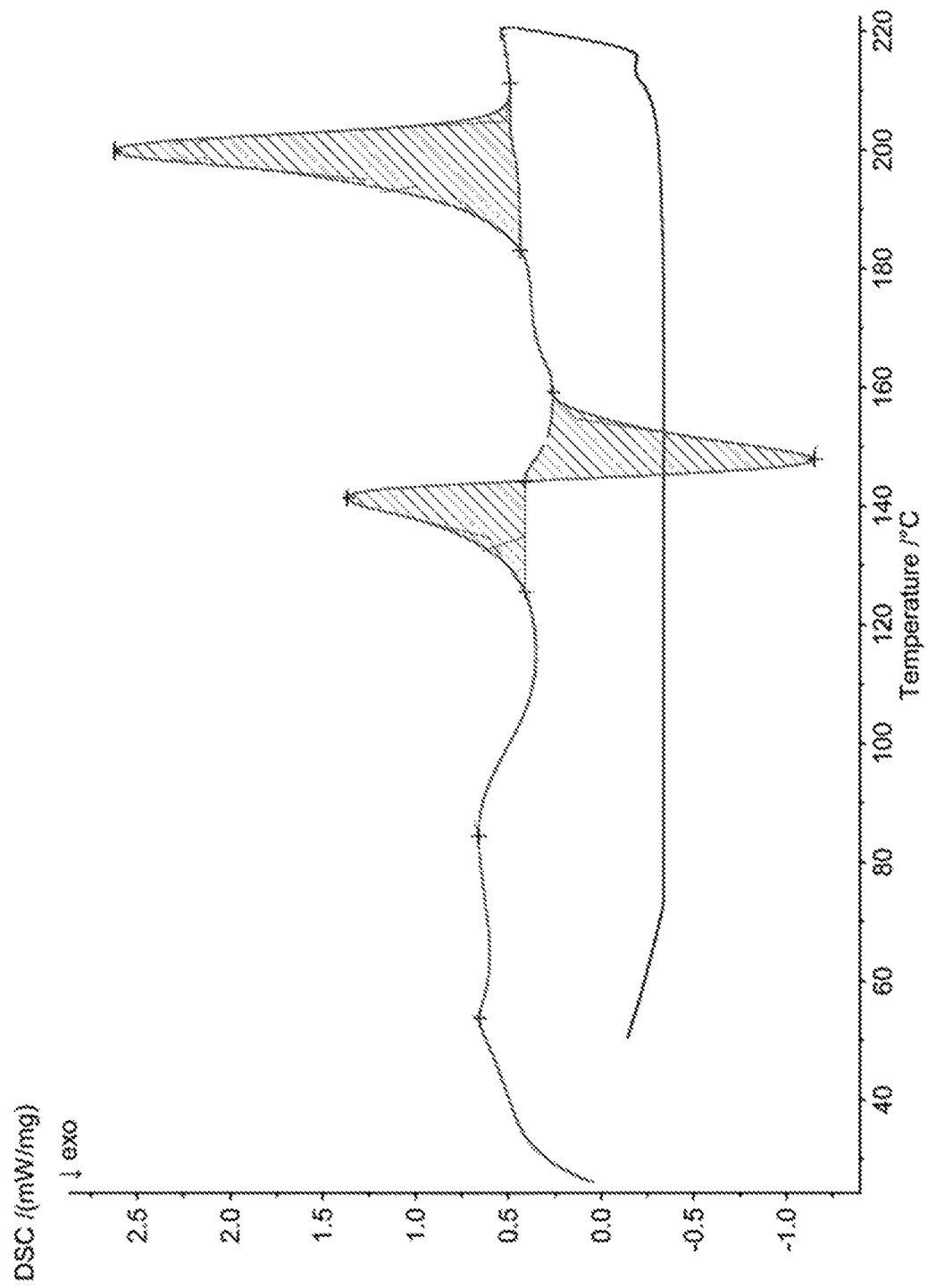
FIG. 13 a DSC-Thermogram of the inventive crystalline Tafamidis meglumine polymorph processed by thermal treatment of amorphous Tafamidis meglumine.

FIG. 13 displays the DSC-curve of the the inventive crystalline Tafamidis meglumine polymorph processed by dispersion/evaporation in pentane/hexane. The DSC reveals a very small endothermic peak at around 141° C., immediately followed by an exothermic transition at 148° C. The crystalline material melts at around 200° C. Therefore, the DSC reveals that the differently processed crystalline material comprises within the error of the experiments very similar phase transitions and melting behaviour.

Figure 14:
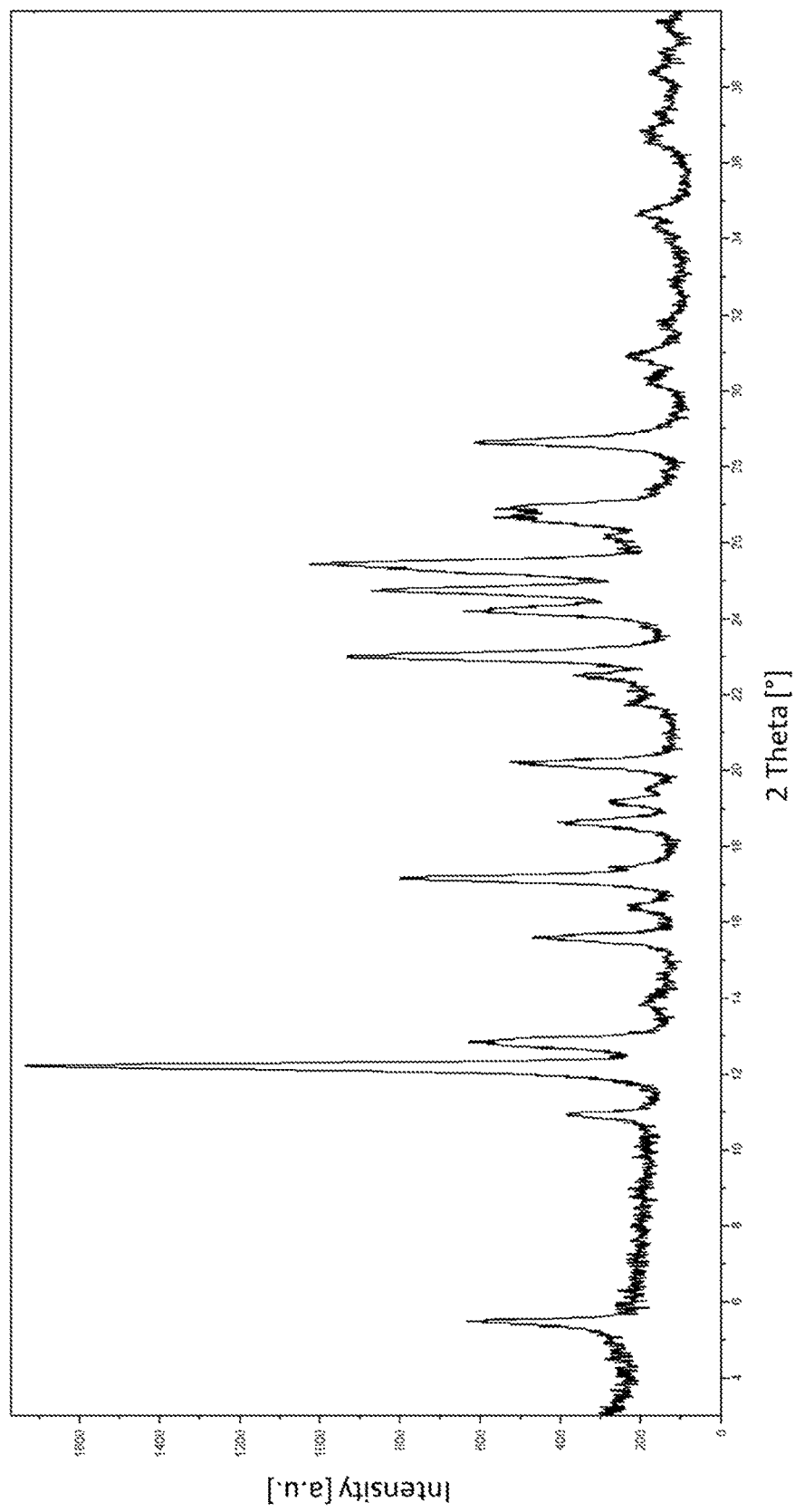
FIG. 14 a PXRD diffraction pattern of a pressure treated crystalline Tafamidis meglumine polymorph processed by dispersion/evaporation in pentane/heptane.

FIG. 14 displays the PXRD diffraction pattern of pressurized crystalline Tafamidis meglumine synthesized according to the inventive route of synthesis. The pressure treatment is described in detail below. The material was processed according to method 1 in pentane/heptane as described below. Within the error of the experiment the diffraction pattern does not change upon pressure treatment, indicating that the inventive crystalline polymorph is stable with respect to prolonged pressure treatments.

| °/2 θ | d-spacing/Å | Intensity (rel.) |
|---|---|---|
| 5.5 | 16.11 | 28 |
| 11.0 | 8.06 | 13 |
| 12.2 | 7.23 | 100 |
| 12.9 | 6.86 | 24 |
| 13.8 | 6.40 | 4 |
| 15.6 | 5.68 | 21 |
| 16.4 | 5.39 | 6 |
| 17.2 | 5.16 | 40 |
| 18.6 | 4.76 | 17 |
| 19.2 | 4.62 | 10 |
| 20.2 | 4.40 | 24 |
| 21.7 | 4.09 | 6 |
| 22.5 | 3.95 | 14 |
| 23.0 | 3.87 | 52 |
| 24.1 | 3.69 | 27 |
| 24.7 | 3.60 | 47 |
| 25.5 | 3.50 | 54 |
| 26.1 | 3.41 | 9 |
| 26.6 | 3.35 | 23 |
| 27.0 | 3.31 | 24 |
| 28.6 | 3.12 | 33 |
| 30.2 | 2.96 | 5 |
| 30.9 | 2.89 | 8 |
| 31.7 | 2.82 | 2 |
| 32.8 | 2.73 | 1 |
| 34.6 | 2.59 | 7 |
| 36.5 | 2.46 | 6 |
| 38.4 | 2.35 | 5 |
| 39.0 | 2.31 | 3 |

Figure 15:
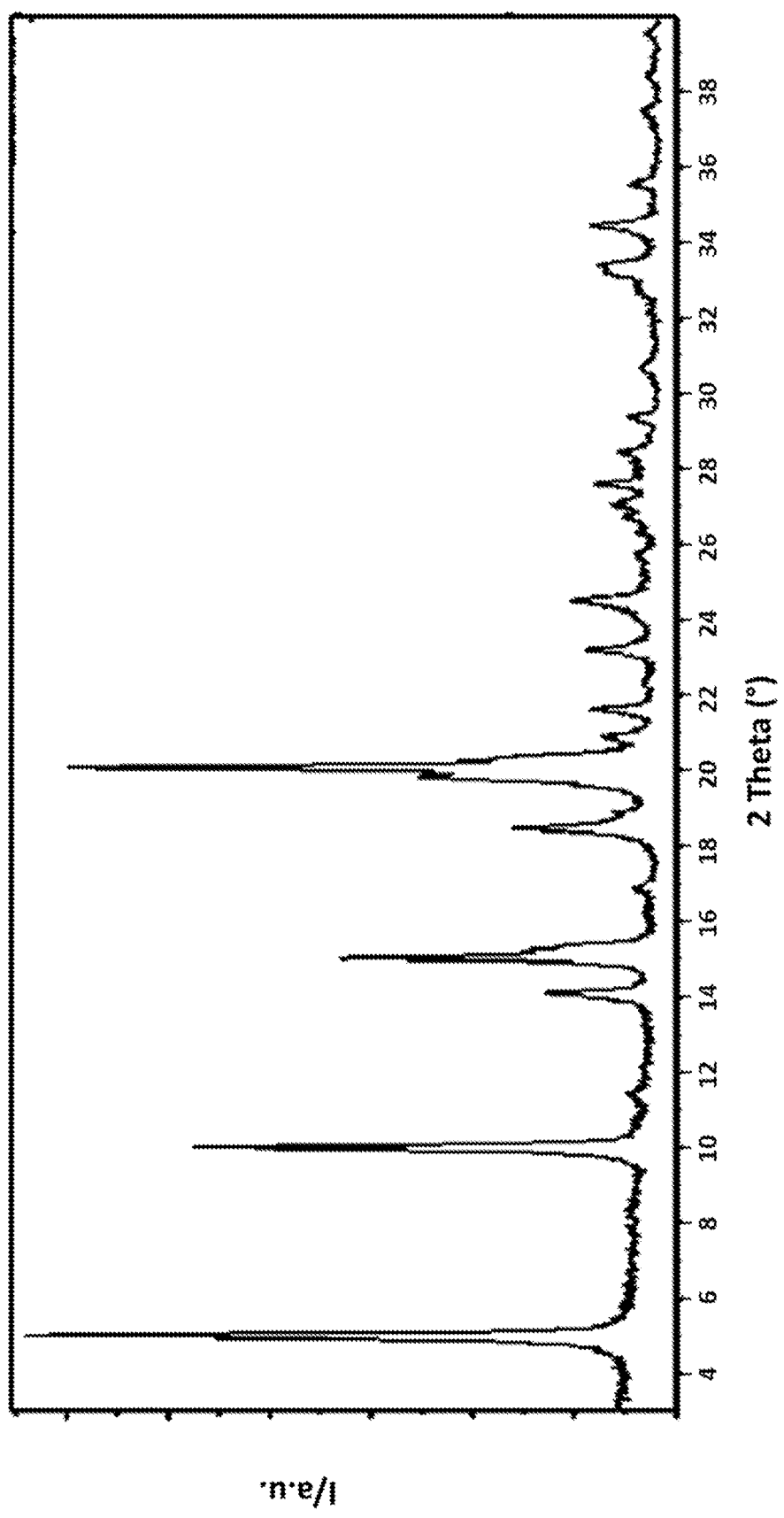
FIG. 15 a PXRD diffraction pattern of crystalline formic acid adduct obtained by the inventive process.

FIG. 15 displays a PXRD diffraction pattern of crystalline formic acid adduct obtained by the inventive process. The PXRD reveals diffraction peaks at

| Pos. (°2theta) | d-spacing (A) | rel. Intensity |
|---|---|---|
| 5 | 17.63 | 100 |
| 10 | 8.83 | 74 |
| 11.4 | 7.76 | 3 |
| 14.1 | 6.28 | 17 |
| 15 | 5.89 | 52 |
| 15.4 | 5.76 | 12 |
| 16.9 | 5.26 | 2 |
| 18.5 | 4.8 | 24 |
| 19.8 | 4.48 | 39 |
| 20.1 | 4.42 | 95 |
| 20.4 | 4.35 | 21 |
| 20.9 | 4.24 | 7 |
| 21.6 | 4.11 | 10 |
| 23.2 | 3.83 | 11 |
| 24.5 | 3.63 | 13 |
| 25.7 | 3.46 | 3 |
| 26.7 | 3.34 | 4 |
| 27 | 3.3 | 6 |
| 27.6 | 3.23 | 10 |
| 28.4 | 3.14 | 6 |
| 29.4 | 3.04 | 4 |
| 30.7 | 2.91 | 3 |
| 33.2 | 2.7 | 8 |
| 33.4 | 2.68 | 8 |
| 34.5 | 2.6 | 10 |
| 35.5 | 2.53 | 4 |
| 37.5 | 2.4 | 2 |
| 38.4 | 2.34 | 1 |
| 39.6 | 2.28 | 2 |

Figure 16:
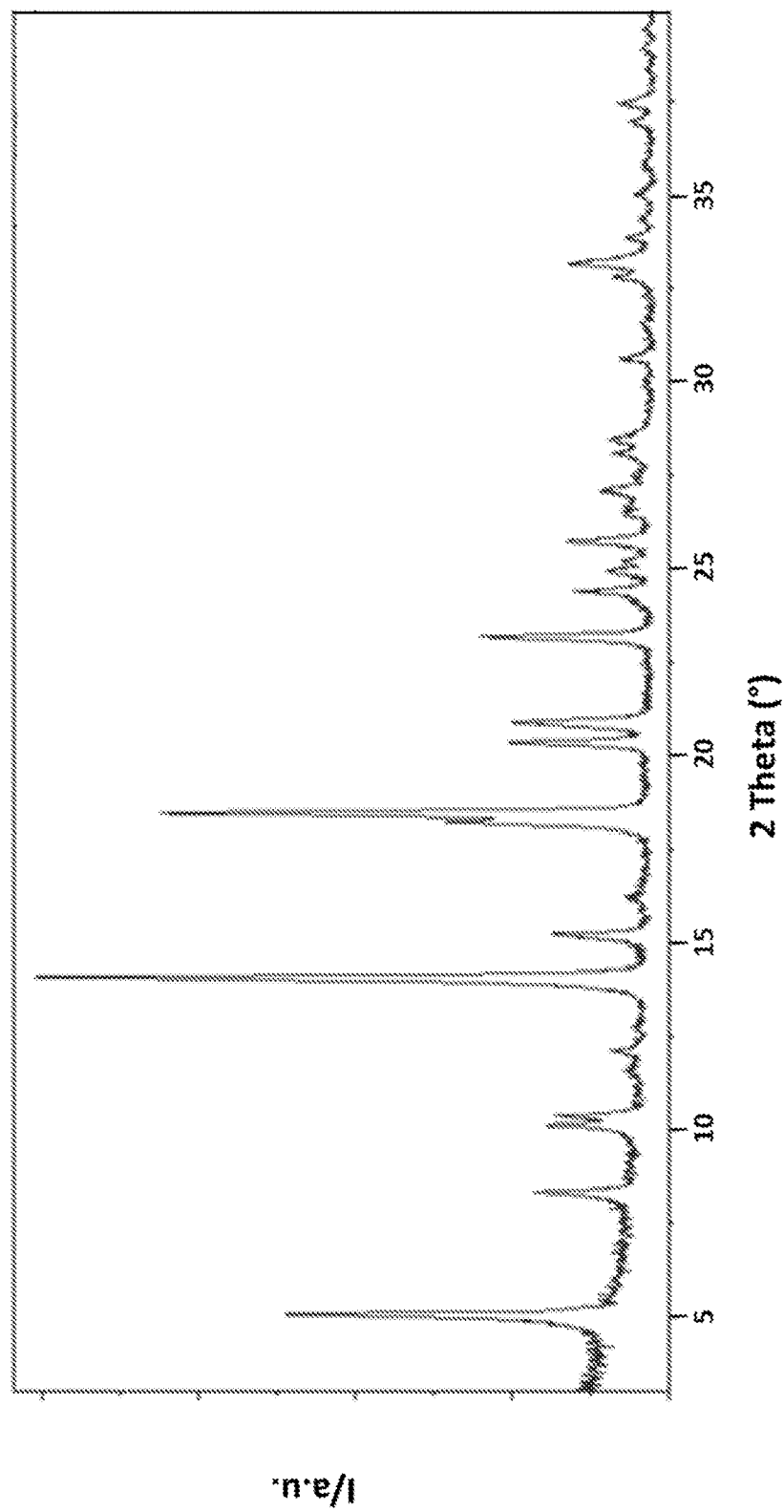
FIG. 16 a PXRD diffraction pattern of crystalline Tafamidis free acid polymorph obtained by the inventive process.

FIG. 16 displays a PXRD diffraction pattern of crystalline Tafamidis free acid polymorph obtained by the inventive process. The PXRD reveals diffraction peaks at

| Pos. (°2theta) | d-spacing (A) | rel. Intensity |
|---|---|---|
| 5.1 | 17.39 | 50 |
| 8.4 | 10.58 | 15 |
| 10.2 | 8.71 | 14 |

-continued

| Pos. (°2theta) | d-spacing (A) | rel. Intensity |
|---|---|---|
| 10.4 | 8.50 | 12 |
| 12.1 | 7.30 | 4 |
| 14.1 | 6.28 | 100 |
| 15.3 | 5.81 | 15 |
| 16.2 | 5.47 | 3 |
| 18.2 | 4.87 | 34 |
| 18.5 | 4.80 | 81 |
| 20.4 | 4.35 | 21 |
| 20.9 | 4.25 | 23 |
| 23.2 | 3.83 | 27 |
| 24.4 | 3.65 | 11 |
| 25.0 | 3.57 | 7 |
| 25.2 | 3.53 | 4 |
| 25.7 | 3.46 | 13 |
| 26.5 | 3.37 | 4 |
| 27.1 | 3.29 | 7 |
| 28.1 | 3.18 | 6 |
| 28.5 | 3.13 | 6 |
| 30.6 | 2.92 | 4 |
| 31.5 | 2.84 | 1 |
| 32.8 | 2.73 | 6 |
| 33.2 | 2.70 | 13 |
| 33.8 | 2.65 | 4 |
| 34.4 | 2.61 | 1 |
| 35.0 | 2.56 | 2 |
| 35.8 | 2.51 | 1 |

Figure 17:
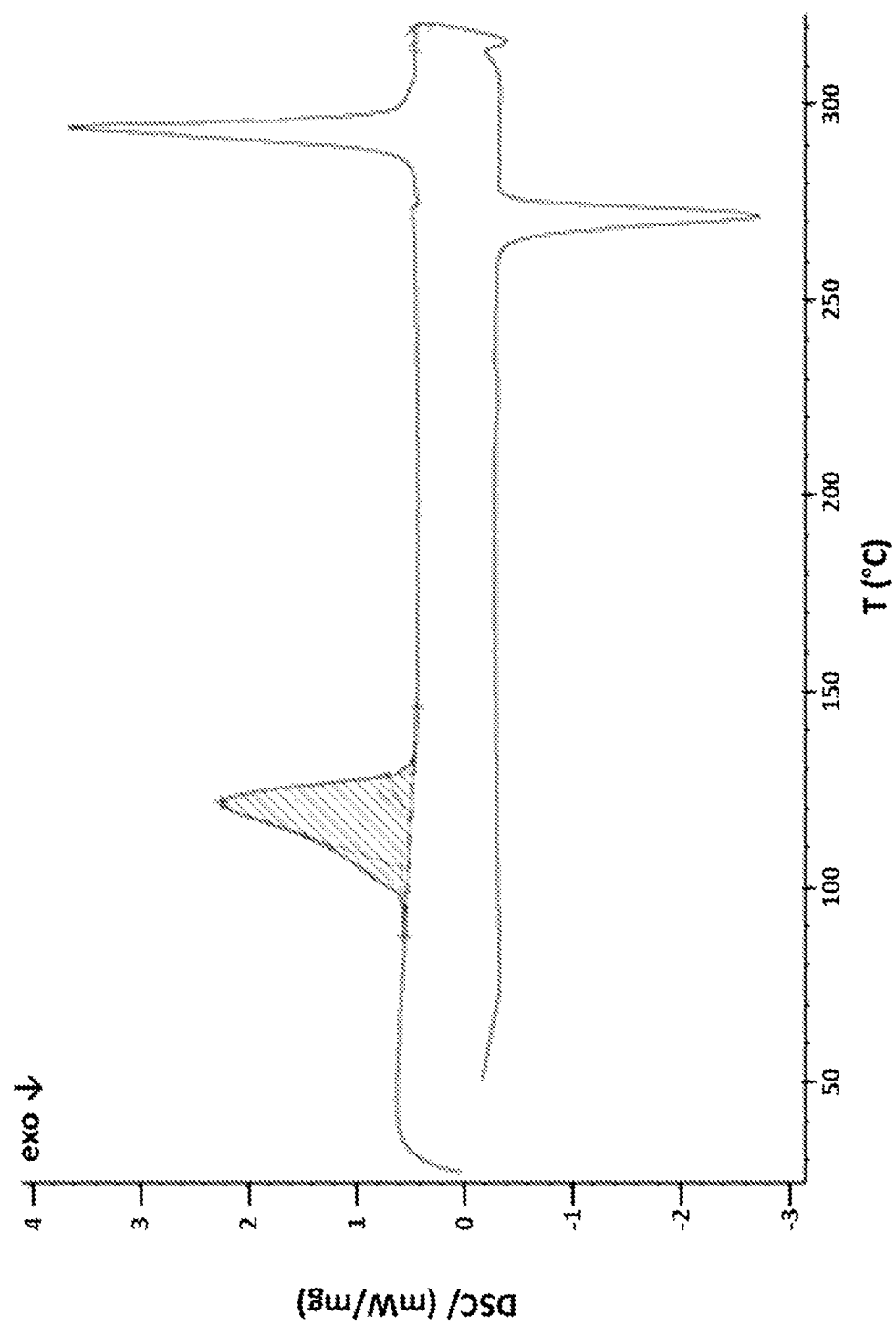
FIG. 17 a DSC-Thermogram of the inventive crystalline Tafamidis formic acid adduct.

FIG. 17 shows a DSC-Thermogram of the inventive crystalline Tafamidis formic acid adduct. The thermogram displays a distinct endothermic peak starting at 105° C. Two further peaks are obtained at approximately 300° C. (endo) and at approximately 270° C. (exo).

EXPERIMENTAL EXAMPLES

I. Methods
PXRD-Measurements

The diffraction measurements were performed at ambient conditions on a PANalytical X'Pert PRO θ-θ diffractometer of 240 mm of radius in reflection geometry, equipped with Cu Kα radiation and a PIXcel detector, operated at 45 kV and 40 mA. Each sample was mounted on a zero-background silicon holder and allowed to spin at 0.25 rev/s during data collection. The measurement angular range was 3.0-40.0° (2θ) with a step size of 0.013°. The scanning speed was 0.0821°/s (40.80 s/step).

DSC-Measurements

DSC measurements were carried out using a 204 F1 Phoenix (NETZSCH) DSC device. The analyzer used a nitrogen purge gas with a rate of flow of 20 mL/min, and 25 µL aluminium pans with pin holes were used for the entire study. The DSC was calibrated for temperature and sensitivity at the same scan rates used in the study with reference materials having transitions in the range of interest. Heating parameters are the following: Initial temperature—Room temperature, 25° C., equilibrate 3 min. Heating up to 220° C., heating rate: 10K/min. Cooling to 40° C., cooling rate: 10K/min. Sample size: 10-20 mg. Nitrogen was used as the purge gas and the protective gas with a rate of flow of 20 mL/min for each line for the whole measurement.

Pressure Set-Up

Dry samples were pressed at the indicated pressures in a Perkin Elmer hydraulic press using a 13 mm stamp for a time period of 3-5 seconds.

II. Route of Synthesis

Pre-Step—Compound B: 3,5-dichlorobenzoyl chloride 10.0 g (0.0524 mole, 1.0 eq.) of 3,5-dichlorobenzoic acid was suspended in 300 ml of toluene. 10.0 ml (0.136 mole, 2.6 eq.) $SOCl_2$ and 1.0 ml (catalytic amount) of DMF were added to the suspension and heated to reflux for 3 hours. The toluene was distilled of by a vacuum distillation to give dark brown oil. The yield was 100% and compound B was used without further purification.

Step 1—Compound D: 4-[(3,5-dichlorobenzoyl) amino]-3-hydroxy-benzoic acid

Method I

In a 2000 ml round bottom flask 8.17 g 4-amino-3-hydroxy-benzoic acid was dissolved in 300 ml THF at room temperature (24° C.). Pyridine (5 ml) was added to the solution and the mixture was cooled with an ice-salt bath to −12° C. Diluted 3,5-dichlorobenzoyl chloride (0.0524 mole in 50 ml THF) from the pre-step was added to the reaction mixture at −5° C. during 10 min. The reaction is exothermic and the reaction temperature was controlled around 0° C. After complete addition of the benzoyl chloride the reaction mixture was stirred for 40 min and the temperature decreased form room temperature down to −10° C. The cooling was stopped and the reaction mixture was allowed to warm to 10° C. under stirring. To the mixture 650 ml of 0.2 M HCl aqueous solution was added and resulted in precipitation. Another portion of HCl solution (400 ml, 0.2 M aqueous) was added and the slurry was stirred overnight at room temperature (24° C., pH 1-2). The precipitate was filtered and the filter cake was washed with 500 ml deionized water until the pH of filtrate was neutral. After drying of filter cake 15 g crude product was obtained which was then purified for the next steps.

Further Purification of Compound D

The crude intermediate D (15 g, HPLC purity 93%) was quenched with 400 ml 0.5 M NaOH aqueous solution and stirred at room temperature (21° C.) for 20 min. The solution was filtered and the filtrate was extracted with 200 ml of DCM. The organic layer was separated and the aqueous layer was filtered and after that the pH was adjusted with 1 M HCl solution (~200 ml) until pH ~2-3. A milky white precipitate formed which was filtered and washed with 300 ml deionized water. The filter cake was dried in a drying oven at 85° C. 100 mbar overnight. Drying results in 13.3 g of compound D with 95.8% purity (HPLC).

In a 1000 ml round bottom flask intermediate D (13.3 g, HPLC purity 95.8%) was suspended in 500 ml 1-butanol. The solution was heated to reflux (115° C.) for 7 hours. After that the slurry was cooled to 70° C. and stirred additionally overnight at 70° C. Hot filtration was performed and the filter cake was washed with 100 ml of hot 1-butanol. The solid was dried in a vacuum oven at 80° C. and 100 mbar overnight. 10.56 g of a grey solid was obtained after drying. Yield: 60.3%.

Method II

In a 2000 ml round bottom flask 6.67 g 4-amino-3-hydroxy-benzoic acid was dissolved in a mixture of THF (126 ml) and water (12.6 ml) at room temperature (24° C.). The 3,5-dichlorobenzoyl chloride (1.2 eq.) was added within 20-30 minutes to the reaction mixture at 20° C. and stirred for an hour. 1.2 eq. of trimethylamine was added to the reaction mixture and stirred for further 30 min. The reaction mixture was charged with 1000 ml 0.1M HCl aq. solution. A precipitate formed and was filtered by vacuum filtration. The obtained filter cake was washed with water. The wet filter cake was dissolved in 300 ml of 0.5 M NaOH aq. solution and was filtered in order to separate insoluble particles. The mother liquor was washed with DCM and neutralized with 1 M HCl aq. solution until pH=7-8. The formed slurry was charged with acetonitrile and filtered by vacuum filtration. The filter cake was intensively washed with deionized water and dried in oven at 90° C. in vacuum. 9.15 g of white solid was prepared (Yield: 64.4%). The dry intermediate D can be used without further purification.

Step 2—Compound E: Tafamidis Acetic Acid Adduct 10.56 g (0.0324 mole, 1.0 eq.) of 4-[(3,5-dichlorobenzoyl) amino]-3-hydroxy-benzoic acid (compound D) was suspended in 600 ml glacial acetic acid. 30.80 g (0.162 mole, 5.0 eq.) pTsOHxH$_2$O (p-Toluenesulfonic acid×H$_2$O) was added and heated to reflux for 2 hours. A condenser was attached and 450 ml of acetic acid was distilled in six hours. The reaction mixture was allowed to cool overnight. The crude mass was filtered off and the filter cake was washed with 15 ml acetic acid. The filter cake was dried overnight at 50° C. and 100 mbar. After drying 10.3 g of product was obtained which was charged with 750 ml glacial acetic acid. 370 mL of the acetic acid was distilled of and after that the turbid solution was allowed to cool to room temperature overnight. The resulting precipitate was filtered and the filter cake was dried in a vacuum oven at 50° C. and 100 mbar. 9.54 g product was isolated as white needles. The yield was 9.54 g (80.0%) and the purity was 99.6% (HPLC). The product comprise a phase transition followed by melting around 298-303° C.

Step 3—Compound F: Tafamidis Meglumine—Amorphous

Method 1

0.500 g Tafamidis*CH$_3$COOH solvate was dispersed in 150 ml 1-butanol and heated to reflux. The reaction mixture is boiling at 112-113° C. and a clean transparent solution was obtained. A distillation condenser was attached to the reaction flask and the butanol was distillated until approximately 7 ml residual volume remained. 0.265 g of D-Meglumine was dissolved in 20 ml water and added to the reaction mixture. An emulsion formed and was refluxed for 15 min (Boiling point 90° C.) and allowed to cool to room temperature (24° C.). The cooled reaction mixture was filtered and the mother liquor was evaporated by a rotavapor at 50° C. and 150-30 mbar until a gel-like mass formed. The gel-like mass was removed to a beaker and after that dried overnight in drying oven at 25° C. 50 mbar. The formed solid was grinded and stored overnight in drying oven at 50° C. The Chemical yield was 6 g (87.8%) and the material showed a phase transition followed by melting at 200-202° C.

Method 2

9.0818 g Tafamidis*CH$_3$COOH solvate was suspended in 3000 ml EtOAc and heated to 65° C. until a transparent solution was obtained. The solution was cooled to 30-32° C. and was 10 times washed with 1000 ml deionized water. The resulting ~2000 ml EtOAc solution was charged with MeOH/H$_2$O solution (1000 ml MeOH/150 ml H$_2$O). 4,8155 g D-Meglumine was dissolved in 40 ml H$_2$O and added at room temperature to a MeOH/H$_2$O mixture (1000 ml MeOH/150 ml H$_2$O 34° C.). The monophasic transparent solution was heated to 50° C. and was concentrated under reduced pressure to approximately 2000 ml target volume. The concentrated reaction mixture was cooled to 32-34° C. and filtered via gravity filtration with a funnel and a filter paper. The mother liquor was evaporated at 50° C. and 200 mbar via rotavapor until a gel-like mass was obtained. The residual gel was removed to a beaker and stored for 3 days in oven at 25-27° C. and 100 mbar. The dried product was grinded and stored overnight at 50° C. and 100 mbar. The chemical yield was 11.33 g (91.2%) and the purity was 99.98% (HPLC). The product shows a phase transition followed by melting at 298-303° C.

Crystalline Form I—A (Melting)

The dried amorphous product was melted in a drying oven for a short time at 85° C. A short time interval is in between 2 hours and 5 hours. The heating was performed using a timer and the heating started from RT. Excess water, if present, can be further removed in vacuum. The product looked like caramel and was removed from the oven after cooling to room temperature.

Crystalline Form I—B (Suspension/Drying)

Method 1 (Pentane/Heptane)

1.53 g amorphous Tafamidis meglumine prepared according to the invention was suspended in pentane and the slurry was grinded using a mortar and pestle. The slurry was removed to a round bottom flask equipped with thermometer, reflux condenser and heated to reflux by an oil bath (external bath temperature 45° C.). A distillation condenser was attached and the pentane was distillated under periodic addition of pentane. The dispersion was refluxed for 4 hours at 33° C. and after that the slurry was charged with 100 ml pentane. After 5 hours of distillation the slurry was filtered and the filter cake was suspended in n-heptane and heated overnight to 50° C. (external bath temperature 53-54° C.). The slurry was filtered and dried overnight in oven at 50° C. and 100 mbar. The slurry was filtered and the filter cake was dried in oven for 14 hours at 50° C.

Method 2 (Pentane/Hexane)

0.2 g amorphous Tafamidis meglumine was suspended in 20 ml of pentane and heated to reflux (oil bath temperature 50° C.). Approximately 15 ml pentane was evaporated during refluxing. 10 ml of pentane was added to the slurry and heated again to reflux until approximately 10 ml were evaporated. 50 ml pentane were added and removed by a rotavapor to dryness at 40° C. and 300 to 30 mbar). 20 ml hexane were added to the dry product and heated to reflux (85° C., oil bath) to allow the evaporation of the hexane in order to achieve approximately a 4 ml concentrate. This slurry was dried by an rotavapor to dryness at 40° C. and 300 to 30 mbar followed by drying in a binder at 50° C. and 100 mbar.

Crystalline Form of Tafamidis Meglumine Starting from the Acetic Acid Adduct

This synthesis starts from the Tafamidis acetic acid adduct by reaction with 2 eqv of D-Meglumine. 1 eqv. of Intermediate E (Tafamidis acetic acid adduct) and 2 eqv. of N-Methyl-D-Glucamine were suspended in 6.58 L/kg of MeOH/H$_2$O in a volume ratio of 9:1. The slurry was heated at T=75° C. until the mixture refluxes. The slurry was maintained at reflux conditions for 4-6 hours. The reaction mixture was cooled to 20-25° C. and filtered by vacuum. The filter cake was washed 3 times with 1.8 L/kg MeOH. The filter cake is dried in vacuum at 85° C. overnight. The crude product may be recrystallized with 62.5 L/kg of MeOH/H$_2$O-9:1, if necessary.

A similar set-up can also be used on a smaller scale. 4.55 g (1 eq.) Tafamidis acetic acid adduct and 4.82 g D-meglumine (2 eq.) were suspended in 65 ml MeOH/H₂O-9:1. The slurry was heated to reflux for 6 hours. The slurry was allowed to cool to room temperature and stirred overnight. The slurry was filtered by vacuum and the filter cake was washed with 2 two time 15 ml of MeOH/H₂ O-9:1 and dried overnight in oven at 85° C. Yield: 6.04 g (97%), Volumetric Yield: 93 g/L; HPLC: 100%; NMR: Taf: Megl—1:1, Acetic acid—0%; GC: MeOH—77 ppm; KF: H₂O—0.15%.

Crystalline Form of Tafamidis Formic Acid Adduct Starting from the Acetic Acid Adduct 4.7 g of Tafamidis acetic acid adduct was suspended in 1800 ml formic acid and the slurry was heated to reflux until the slurry disappeared. The clean transparent solution was cooled to RT and stored at that conditions overnight. The crystalline precipitate was vacuum filtered and dried under vacuum at 20° C. for 2 days.

Crystalline Form of Tafamidis Trifluoroacetic Formic Acid (TFAA) Adduct Starting from the Acetic Acid Adduct 1.125 g of Tafamidis Acetic acid adduct was charged with 20 ml of trifluoracetic acid and heated to reflux until the slurry disappeared. The transparent solution was cooled to RT and stored at that conditions overnight. A crystalline compound precipitated, was filtered and dried in vacuum at 20° C. for 2 days.

Crystalline Form of Tafamidis Free Acid Starting from the Acetic Acid Adduct 1.0 g Tafamidis Acetic acid adduct was charged with 100 ml of EtOAc and 20 ml of water. The slurry was heated to reflux until the slurry disappeared. The formed clean biphasic solution was refluxed for 3 hours and allowed to cool to room temperature. The solution was stored at room temperature overnight. The obtained crystals were filtered by vacuum and dried under hood at RT.

Pressure Resistance Crystalline Form

The dried filter cake obtained by the above described method 1 was pressed for 3-5 seconds at 1.5 MPa using a Perkin Elmer hydraulic press and 13 mm tableting stamp. The resulting material was subjected to a DSC and a PXRD-experiment. The results are depicted in FIG. 13 (DSC) and FIG. 14 (PXRD). A comparison between the pressure and the non-pressure form reveals, that the structure of the crystalline form is insensitive to pressure. This feature renders this polymorph suitable for processing in the course of tableting, especially.

What is claimed:

1. A process for the production of a crystalline Tafamidis polymorph, at least comprising the steps of:
   a) Forming a dispersion by contacting a Tafamidis acetic acid adduct (E) and a solvent capable of removing the acetic acid adduct molecule from the Tafamidis;

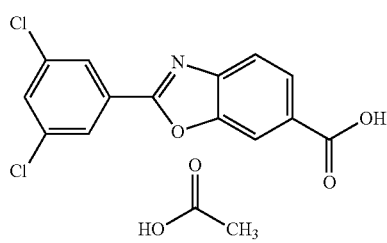

E b) Heating the dispersion obtained in step a) and
   c) Precipitation and drying of the precipitate to yield the crystalline Tafamidis polymorph.

2. The process according to claim 1, wherein the solvent is selected from the group consisting of water, methanol, ethanol, ethylacetate, pentane, hexane, halogenated or non-halogenated formic acid, halogenated or non-halogenated acetic acid or mixtures of at least two solvents thereof.

3. The process according to claim 1, wherein the solvent is a mixture of ethyl acetate and water and the resulting crystalline Tafamidis polymorph is crystalline Tafamidis free acid.

4. The process according to claim 1, wherein the solvent is formic acid and the resulting crystalline Tafamidis polymorph is crystalline Tafamidis formic acid adduct.

5. The process according to claim 1, wherein the solvent is trifluoroacetic acid and the resulting crystalline Tafamidis polymorph is crystalline Tafamidis trifluoroacetic acid adduct.

6. The process according to claim 1, wherein in step a) besides the solvent a further adduct molecule is added to the dispersion.

7. The process according to claim 6, wherein in step a) meglumine is added to the dispersion in step a) and the resulting crystalline Tafamidis polymorph is crystalline Tafamidis meglumine adduct (F).

8. The process according to claim 1, wherein the Tafamidis acetic acid adduct (E) in step a) is obtained by cyclization of 4-(3,5-dichlorobenzamido)-3-hydroxybenzoic acid (D) in the presence of acetic acid and a sulfonic acid

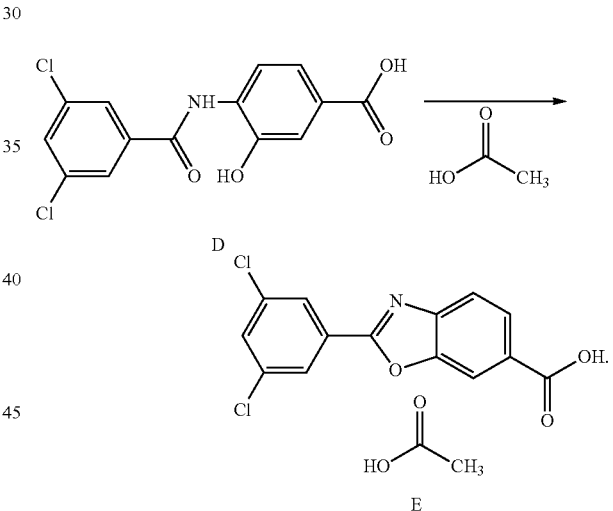

9. The process according to claim 8, wherein the sulfonic acid in the cyclization reaction step a) is p-toluenesulfonic acid.

10. The process according to claim 1, wherein the temperature in the steps a)-c) is maintained below 125° C.

11. A crystalline Tafamidis free acid polymorph, wherein the crystalline form comprises peaks at diffraction angles of 5.1, 14.1, and 18.5 (2θ±0.2 respectively) in a powder X-ray diffraction pattern.

12. A crystalline Tafamidis acetic acid adduct, wherein said crystalline form comprises peaks at diffraction angles of 12.2, 23.0 and 25.5 (2θ±0.2 respectively) in a powder X-ray diffraction pattern.

13. A crystalline Tafamidis formic acid adduct, wherein the crystalline form comprises peaks at diffraction angles of 5.0, 10.0, and 20.1 (2θ±0.2 respectively) in a powder X-ray diffraction pattern.

14. A crystalline Tafamidis meglumine, wherein said crystalline form comprises peaks at diffraction angles of 12.2, 23.0 and 25.5 (2θ±0.2 respectively) in a powder X-ray diffraction pattern.

15. A pharmaceutical composition comprising crystalline Tafamidis meglumine according to claim 14.

16. The pharmaceutical composition according to claim 15, wherein the pharmaceutical composition is an oral dosage form.

17. A method for treating familial amyloid polyneuropathy (FAP), familial transthyretin (TTR) amyloidosis or transthyretin (TTR) familial amyloid polyneuropathy (FAP) with the pharmaceutical composition according to claim 15.

\* \* \* \* \*